(12) United States Patent
Cummings et al.

(10) Patent No.: US 7,273,754 B2
(45) Date of Patent: Sep. 25, 2007

(54) CORE 1 β3-GALACTOSYLTRANSFERASE SPECIFIC MOLECULAR CHAPERONES, NUCLEIC ACIDS, AND METHODS OF USE THEREOF

(75) Inventors: Richard D. Cummings, Edmond, OK (US); Tongzhong Ju, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 481 days.

(21) Appl. No.: 10/661,049

(22) Filed: Sep. 12, 2003

(65) Prior Publication Data

US 2005/0037477 A1    Feb. 17, 2005

Related U.S. Application Data

(60) Provisional application No. 60/411,310, filed on Sep. 13, 2002.

(51) Int. Cl.
*C12N 5/10* (2006.01)
*C12N 15/00* (2006.01)
*C12N 9/10* (2006.01)
*C12N 1/20* (2006.01)
*C12Q 1/48* (2006.01)
*C12P 21/06* (2006.01)
*C07K 14/00* (2006.01)
*C07H 21/04* (2006.01)

(52) U.S. Cl. .................. 435/325; 435/320.1; 435/69.1; 435/15; 435/252.3; 435/193; 536/23.1; 536/23.2; 536/23.5; 530/350

(58) Field of Classification Search .................. 435/15, 435/69.1, 320.1, 252.3, 325, 193; 536/23.1, 536/23.2, 23.5; 530/350
See application file for complete search history.

(56) References Cited

U.S. PATENT DOCUMENTS 6,492,152 B1    12/2002  Canfield et al.
6,635,468 B2    10/2003  Ashkenazi et al.

FOREIGN PATENT DOCUMENTS

WO    WO 00/15796    *  3/2000
WO    WO 2001/40466 A2    6/2001

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E., Molecular Biotechnology 7:253-265, 1997.*
Philips, A., J. Pharm. Pharmacology 53:1169-1174, 2001.*
Gardlik et al., Med. Sci. Monit. 11(4):RA110-121, 2005.*
Current Protocols in Molecular Biology, Hybridization Analysis of DNA Blots, pp. 2.10.8-2.10.11, 1993.*
Berger, E. G., "Tn-syndrome", *Biochim Biophys Acta* 1455, (1999) 255-268.
Brockhausen, I., et al., "Enzymatic basis for sialyl-Tn expression in human colon cancer cells", *Clycoconj J* 15, (1998) 595-603.
Ju, T., et al., "Cloning and Expression of Human Core 1 β1,3-Galactosyltransferase", *J Biol Chem* 277, (2002) 178-186.
Ju, T., et al., "Purification, Characterization, and Subunit Structure of Rat Core 1 β1,3-Galactosyltransferase", *J Biol Chem* 277, (2002) 169-177.
McEver, R. P., et al., "Perspectives Series: Cell Adhesion in Vascular Biology", *J. Clin Invest* 100, (1997) 485-491.
Novak, J., et al., "Progress in Molecular and Genetic Studies of IgA Nephropathy", *J Clin Immunol* 21, (2001) 310-327.
Piller, V., et al., "Biosynthesis of Truncated O-Glycans in the T Cell Line Jurkat", *J Biol Chem* 265, (1990) 9264-9271.
Springer, G. F., "Immunoreactive T and Tn epitopes in cancer diagnosis, prognosis, and immunotherapy", *J Mol Med* 75, (1997) 594-602.
Wells, L., et al., "Dynamic O-Glycosylation of Nuclear and Cytosolic Proteins", *J Biol Chem* 277, (2002) 1755-1761.

* cited by examiner

*Primary Examiner*—Delia M. Ramirez
(74) *Attorney, Agent, or Firm*—Dunlap, Codding & Rogers, P.C.

(57) ABSTRACT

Core 1 β3-galactosyl transferase specific molecular chaperones (Cosmc-1) and nucleic acids encoding the core 1 β3-galactosyl transferase specific molecular chaperones or proteins having core 1 β3-galactosyl transferase specific molecular chaperone activity are described. The polynucleotides encoding Cosmc-1 can be used to transform or transfect host cells for producing substantially pure forms of active forms of core 1 β3-galactosyl transferase and/or for use in an expression system for post-translational core 1 glycosylation of proteins or peptides produced within the expression system, for example, glycosylation via a β3-linkage, of an N-acetylgalactosamine linked to a serine, threonine or other linking amino acid on peptides or proteins requiring O-, N-, or S-linked glycosylation.

5 Claims, 7 Drawing Sheets

FIG. 1A 466 491

Molt-4 Cell

TAAAGTATTTTTTGTTAAAAAAGGAT

K562 Cell

TAAAGTATTTTTTGTTAAAAAAGGAT

Jurkat Cell

TAAAGTATTTTTGTTAAAAAAGGATC

Human K562 cells and Molt-4 Cells

Human Jurkat Cells     *T-deletion*

```
-T-A-A-G-T-A-  -T-T-T- ▮ -T-G-T-T-A-A-
T ——K——Y——F ——————C——STOP
```

FIG. 5

CORE 1 β3-GALACTOSYLTRANSFERASE SPECIFIC MOLECULAR CHAPERONES, NUCLEIC ACIDS, AND METHODS OF USE THEREOF

CROSS-REFERENCE TO RELATED APPLICATIONS

This application claims the benefit under 35 U.S.C. § 119(e) of U.S. Provisional Application Ser. No. 60/411,310, filed Sep. 13, 2002, entitled "Core 1 β3-Galactosyltrasferase Specific Molecular Chaperone-1 and Methods of Use", the contents of which is expressly incorporated herein in its entirety by reference.

STATEMENT REGARDING FEDERALLY FUNDED RESEARCH

Some aspects of this invention were made in the course of NIH Grant AI48075; the U.S. Government has certain rights to this invention.

BACKGROUND

The present invention is related to core 1β3-galactosyl transferase specific molecular chaperones ("Cosmc-1"), and nucleic acids encoding the Cosmc-1 proteins, and to methods of use thereof.

The O-glycans in human glycoproteins and mucins are important in many aspects of cellular metabolism and cellular interactions, including those involved in leukocyte trafficking (1,2). The biosynthesis of mucin-type O-glycans in animal mucins and other glycoproteins is orchestrated by a set of N-acetylgalactosaminyl-transferases that transfer GalNAc to specific serine and threonine (Ser/Thr) residues to generate the sequence GalNAcα1-Ser/Thr, also known as the Tn antigen (3). Subsequently, this precursor is acted upon by the core 1 β3-galactosyltransferase (C1β3Gal-T) to generate the core 1 disaccharide O-glycan Galβ1-3Gal-NAcα1-Ser/Thr (4,5), also known as the T antigen or Thomson-Friedenrich antigen. Unlike most glycosyltransferases, which occur in gene families, a single human gene on 7p14-p13 encodes the C1β3Gal-T (4). Other core structures for mucin-type O-glycans are known, but core 1 is the common core structure found on human erythrocytes and most lymphocytes and it serves as a precursor for the branched core 2 O-glycans Galβ1-3(GlcNAcβ1-6)Gal-NAcα1-Ser/Thr found on human leukocytes (6). The factors regulating expression of core 1 are being intensely studied, since expression of Tn antigen is recognized as a tumor-associated antigen for breast and colon carcinomas (7,8), and the inability to generate the core 1 O-glycan is potentially a contributing factor to several autoimmune diseases, including IgA nephropathy (9), Tn-Syndrome (10), and Henoch-Schönlein purpura (11).

The human T leukemic cell line Jurkat cells lack C1β3Gal-T activity and generates truncated O-glycans bearing the Tn antigen (12, 13). Thus, a potential alteration in the expression of the C1β3Gal-T is predicted to have global changes on the O-glycan structures in multiple glycoproteins. As a result, there has remained a need in the field for complete identification of all steps and requirements for formation of fully active core 1 β3-galactosyl transferase. Such a need is hereby fulfilled as demonstrated hereinbelow.

BRIEF DESCRIPTION OF THE DRAWINGS

FIG. 5 is a comparison of amino acid sequences of human, rat, mouse, and zebrafish Cosmc-1 (SEQ ID NO: 1, SEQ ID NO:7, SEQ ID NO: 3, and SEQ ID NO:5 respectively).

SUMMARY OF THE INVENTION

Figure 1B:
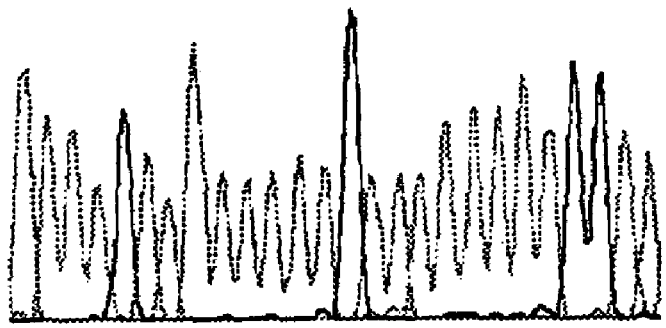
FIG. 1 depicts human Cosmc-1 cDNA and a deduced protein sequence and a mutated Cosmc-1 sequence from human Jurkat cells. (A) The amino acid sequence (SEQ ID NO: 1) and nucleotide sequence (SEQ ID NO: 2) of human Cosmc-1 are shown. The cDNA predicts a 318aa protein with a type-II topology. The putative transmembrane domain is double underlined. The portions of the sequence that correspond to the identified N-terminal sequence copurified with the purified rat liver C1β3Gal-T (5) are indicated by the single underlining. A potential N-glycosylation site is boxed. The asterisk denotes the position of the T-deletion (Jurkat mutation) described below. (B) The cDNA sequence of Cosmc-1 was obtained by RT-PCR using total RNA from Jurkat, Molt-4 and K562 cells. The arrow indicates that portion of the sequence with a T-deletion at bp 478. (C) The T-deletion mutation at bp 478 in Cosmc-1 from Jurkat cells is indicated by the shaded box causing a truncation and introducing a stop codon. (D) Diagram of the domain organization of wild-type Cosmc-1 (wtCosmc-1) and mutated Cosmc-1 (mCosmc-1) from Jurkat cells.
Figure 1B:
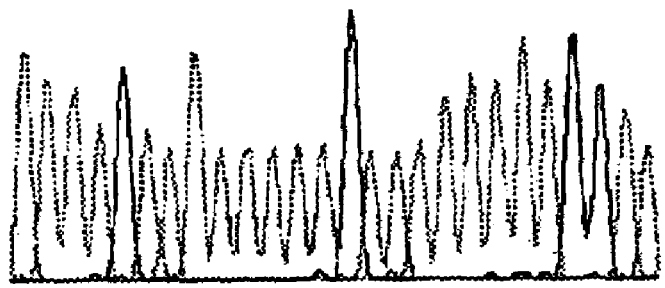
Figure 1B:
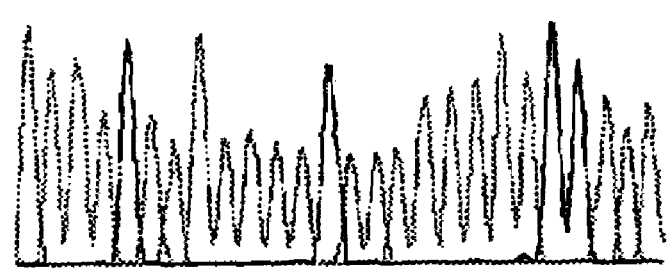
Figure 1C:
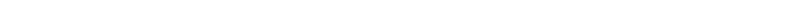

According to the present invention, Core 1 β3-galactosyl transferase Specific Molecular Chaperone-1 (Cosmc-1), nucleic acids encoding Cosmc-1 as well as methods for using same, are provided. Broadly, Cosmc-1 is necessary to create a functional core 1 β3-galactosyl transferase (C1β3Gal-T) wherein co-expression leads to a functional C1β3Gal-T. In one aspect, the invention comprises homologous versions and variants of Cosmc-1 proteins encoded by homologous cDNAs, vectors and host cells which express the cDNAs, and methods of using the Cosmc-1 proteins and cDNAs.

In further aspects, the present invention contemplates cloning vectors which comprise the nucleic acid of the invention, and prokaryotic or eukaryotic expression vectors which comprise the nucleic acid molecule of the invention operatively associated with an expression control sequence. Accordingly, the invention further relates to a bacterial or eukaryotic cell transfected or transformed with an appropriate expression vector.

One object of the present invention is to provide and use a nucleic acid, in particular a cDNA, that encodes a Cosmc-1 or an active fragment thereof, or homologous derivatives or analogs thereof, or proteins having Cosmc-1 activity.

In further aspects of the present invention there is provided recombinant DNA which encode Cosmc-1 or variants thereof, plasmids comprising such DNA and cell lines comprising these plasmids or the recombinant DNA itself such that expression of the Cosmc-1 or variants thereof may be achieved. Such recombinant DNA is conveniently provided by PCR amplification of the DNA encoding for the desired sequence, using primers targeted at respective ends of the double stranded sequence of which it forms one half, using methods well known to those of ordinary skill in the art. The present invention further comprises a Cosmc-1 mutant and polynucleotide encoding the mutant wherein the mutant is truncated at the C-Terminal end and the polynucleotide has a mutation at bp 478.

Furthermore, the present invention provides polyclonal or monoclonal antibodies to the Cosmc-1 or variants or antigenic fragments thereof, of the invention, and hybridoma cells for production thereof as described in more detail below.

The present invention contemplates variants of Cosmc-1 which have conservative substitutions of amino acids therein, such that the mutants or variants of Cosmc-1 continue to be effective as a chaperone to Core 1β3Gal-T, or which induce antigens against Cosmc-1.

A further object of the present invention, while achieving the before-stated object, is to provide a cloning vector and an expression vector for such a nucleic acid molecule.

Yet another object of the present invention, while achieving the before-stated objects, is to provide a recombinant cell line that contains such an expression vector.

Yet a further object of the present invention, while achieving the before-stated objects, is to produce active Cosmc-1 and/or active fragments thereof.

A still further object of the present invention, while achieving the before-stated objects, is to provide methods for using Cosmc-1 and fragments thereof.

Other objects, features and advantages of the present invention will become apparent from the following detailed description when read in conjunction with the appended claims.

DETAILED DESCRIPTION OF THE INVENTION

The core 1 O-linked glycan structure, consisting of galactose in β1,3 linkage to N-acetylgalactosamine linked to a threonine or serine on a protein, peptide or polypeptide, is a critical intermediate in the biosynthesis of most extended O-linked glycans. The core 1 structure is found on a number of mucins and adhesion molecules. Core 1 β3-galactosyl transferase (see for example, U.S. Pat. No. 6,492,152, the entirety of which is hereby expressly incorporated by reference herein) functions to synthesize the core 1 O-linked glycan structure Gal β3-GalNAc-Thr/Ser.

In exploring the factors that regulate C1β3Gal-T activity in Jurkat cells, we identified a novel protein that associates with C1β3Gal-T and is required for its activity. This protein, which has the properties of a chaperone, was designated Cosmc-1 (Core 1 β3-Gal-T Specific Molecular Chaperone-1). Further, shown herein is a mutation in Cosmc-1 in Jurkat cells which results in loss of C1β3Gal-T activity and targeting of the inactive protein to the proteasome. Thus, either inherited or somatic mutations in the gene encoding Cosmc-1, which is localized on the X-chromosome, can contribute to expression of Tn antigen in tumor cells and in human autoimmune diseases.

As shown herein, expression of the active form of C1β3Gal-T requires the co-expression of a unique molecular chaperone protein, Cosmc-1. The Cosmc-1 gene is mutated in human Jurkat cells and encodes a cDNA containing a T deletion resulting in a frame-shift and predicted truncation of the mutated protein. The cDNA encoding Cosmc-1 predicts a protein of about 36.4 kDa and our studies show that Cosmc-1 can associate with C1β3Gal-T.

As contemplated herein, Cosmc-1 is a required co-factor (chaperone) for the generation of a fully active form of C1β3Gal-T since only inactive protein can be generated in insect cells in the absence of Cosmc-1 co-expression. Such a co-factor function is consistent with a chaperone-assisted folding function of Cosmc-1.

Northern blot analysis of Cosmc-1 expression in human tissues reveals that Cosmc-1 expression mirrors that observed for C1β3Gal-T (4) (data not shown), consistent with the role of Cosmc-1 in $\alpha_1\beta_3$Gal-T expression. Several such protein specific chaperones have been identified for other ligands, including HSP47, a collagen-specific molecular chaperone (20), calmegin, which is specific for alpha/beta fertilin (21), the copper chaperone for superoxide dismutase (CCS-1) (22), and many others (23), although Cosmc-1 is the first molecular chaperone known to be required for a specific glycosyltransferase. Some molecular chaperones, such as HSP40, HSP60 and HSP90, interact with proteins to stabilize intrinsically unstable folding intermediates (24, 25).

The Cosmc-1 gene is located on the X-chromosome, indicating relevance to understanding some human diseases that are associated with or result from deficiencies in C1β3Gal-T activity. For example, the Tn antigen is a common marker in many types of tumors (7, 8), indicating that alterations in expression of Cosmc-1 and consequently of C1β3Gal-T may be contributing factors for altered glycosylation by tumor cells. In addition, IgA nephropathy (Berger's disease) is characterized by a decreased galactose content of O-glycans of IgA1 (27-29), which has five potential O-glycosylation sites in the hinge region, in contrast to IgA2, IgM, and IgG, which lack O-glycans in the hinge region. It has been proposed that the galactose deficiency in IgA1 of these patients results from a deficiency in C1β3Gal-T activity (30). IgA nephropathy exhibits a 2:1 male predominance (31), suggesting a possible X-linkage. Results provided herein indicate that mutations in Cosmc-1, either genetically inherited or occurring randomly in a precursor stem cell, can be associated with decreased C1β3Gal-T activity in select B-cell populations responsible for IgA production. Defects in Cosmc-1 expression or in the direct expression of the C1β3Gal-T may also be involved in other diseases associated with expression of Tn antigen, such as Tn syndrome and Henoch-Schönlein purpura.

The expression of recombinant forms of glycosyltransferases is most often accomplished by taking a cDNA which encodes the glycosyltransferase and expressing this cDNA in a host cell, such as Chinese hamster ovary (CHO) cells or other mammalian or vertebrate animal cell lines, or non-vertebrate animal cell lines, such as insect cells or cell lines, or fungal cells or cell lines, or plants or plant cell lines, or yeast, or bacteria. The recombinant enzyme is usually active. However, as described herein, we have discovered that the cDNA encoding the mammalian C1β3Gal-T gives rise to an inactive protein when expressed in non-vertebrate animal and non-mammalian cells or cell lines. Activity requires the co-expression of a cDNA encoding the Cosmc-1 protein. No reports of expression of recombinant mammalian C1β3Gal-T have appeared. This lack of success of making a recombinant form of the mammalian C1β3Gal-T in non-vertebrate animal and non-mammalian cells or cell lines is explained by the absence of Cosmc-1.

Cosmc-1 is encoded in the mammalian and vertebrate genome, but is absent in non-vertebrate animal cells. Some vertebrate or mammalian cell or cell lines either lack Cosmc-1 or have a mutated form of the gene encoding Cosmc-1, either through gene deletion or mutagenesis. These cell lines, such as the human T-cell lymphoblastoid cell line Jurkat, cannot efficiently synthesize C1β3Gal-T protein or enzyme activity, since they lack wild-type Cosmc-1 expression. This defect can be overcome or complemented by co-expressing cDNA encoding Cosmc-1 along with their endogenous C1β3Gal-T enzyme or a recombinant form of the C1β3Gal-T. Thus, the discovery of Cosmc-1, in one embodiment, provides possible new diagnostic tools for identifying those patients having or at risk for certain diseases, and may provide a means of treating or curing the diseases.

The polynucleotides of the present invention may be in the form of RNA or in the form of DNA, wherein the term "DNA" includes cDNA, genomic DNA and synthetic DNA. The DNA may be double-stranded or single-stranded, and if single-stranded, may be the coding strand or non-coding (anti-sense) strand. The coding sequences which encodes the mature polypeptide may be identical to the coding sequences shown herein (e.g., expressible portions of SEQ ID NOs: 2, 4, 6, and 8) or may be variant coding sequences which, as a result of the redundancy or degeneracy of the genetic code, encode the same, mature polypeptide as the DNA coding sequences shown herein or similar polypeptides having Cosmc-1 activity.

The polynucleotides claimed herein which encode the mature polypeptides may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns, or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of the polypeptides having the amino acid sequences of SEQ ID NO:1, 3, 5, or 7. The variants of the polynucleotide may be naturally occurring allelic variants of the polynucleotides or nonnaturally occurring variants of the polynucleotides.

Thus, the present invention includes polynucleotides encoding the same mature polypeptides as shown in SEQ ID NO:1, 3, 5 and 7, as well as variants of such polynucleotides which encode active fragments, derivatives or analogs of said polypeptides. Such nucleotide variants include deletion variants, substitution variants and addition or insertion variants.

As hereinabove indicated, the polynucleotide may have a coding sequence which is a naturally occurring allelic variant of the coding sequences of SEQ ID NO:2, 4, 6, or 8. As is known in the art, an allelic variant is an alternate form of a polynucleotide sequence which may have a substitution, deletion or addition of one or more nucleotides which does not substantially adversely alter or diminish the function of the encoded polypeptide.

The present invention further relates to a Cosmc-1 polypeptide which has the amino acid sequence of SEQ ID NO:1, 3, 5, or 7, as well as fragments, analogs and derivatives of such polypeptide.

The terms "fragment", "derivative" and "analog" when referring to the polypeptide of SEQ ID NO:1, 3, 5, or 7, refer to proteins which retain essentially the same or increased biological functions or activities as the native Cosmc-1. Thus, an analog includes a proprotein which can be activated by cleavage of a proprotein portion to produce an active mature polypeptide. Fragments of Cosmc-1, as described herein, include soluble, active proteins which have the N-terminal transmembrane region removed.

The polypeptide of the present invention may be a natural polypeptide or a synthetic polypeptide, or preferably a recombinant polypeptide.

The fragment, derivative or analog of the polypeptide of SEQ ID NO:1, SEQ ID NO:3, SEQ ID NO:5, or SEQ ID NO:7 as contemplated herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol—PEG), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of one of ordinary skill in the art given the teachings herein.

The polypeptides and polynucleotides of the present invention are preferably provided in an isolated form, and preferably are purified substantially to homogeneity. The term "isolated" means that the material is removed from its original environment (e.g., the natural environment if it is naturally occurring) in a form sufficient to be useful in performing its inherent enzymatic function. For example, a naturally-occurring polynucleotide or polypeptide present in a living animal is not isolated, but the same polynucleotide or polypeptide separated from some or all of the coexisting materials in the natural system, is isolated. Such polynucleotides could be part of a vector, and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention, and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, or a phage or other vectors known in the art. The engineered host cells can be cultured in conventional nutrient media modified as appropriate for activating promoters, selecting transformants or amplifying the Cosmc-1 genes. The culture conditions, such as temperature, pH and the like, are those previously used with the host cell selected for expression, and will be apparent to the ordinary skilled artisan.

The Cosmc-1-encoding polynucleotides of the present invention may be employed for producing Cosmc-1 by recombinant techniques or synthetic in vitro techniques. Thus, for example, the Cosmc-1-encoding polynucleotides may be included along with a gene encoding a core 1 β3-GalT and a gene encoding a protein requiring O-linked glycosylation in any one of a variety of expression vectors for expressing the Cosmc-1, core 1 β3-GalT, and the protein requiring O-linked glycosylation. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable in the host. In one embodiment, the protein requiring O-linked glycosylation is P-selectin glycoprotein ligand-1 or a portion thereof or a synthetic sulfopeptide which has P-selectin binding activity.

The appropriate DNA sequence (or sequences) may be inserted into the vector by a variety of procedures. For example, the DNA sequence may be inserted into an appropriate restriction endonuclease sites(s) by procedures known in the art. Such procedures and others are deemed to be within the scope of a person of ordinary skill in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells, such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein as described elsewhere herein.

As representative examples of appropriate hosts, there may be mentioned: bacterial cells, such as E. coli, Streptomyces, Salmonella typhimurium; fungal cells, such as yeast; insect cells such as Drosophila and Sf9; animal cells such as CHO, COS, 293T or Bowes melanoma; or plant cells. The selection of an appropriate host is deemed to be within the scope of a person of ordinary skill in the art given the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Bacterial: pQE70, pQE60, pQE-9 (Qiagen), pbs, pD10, phagescript, psiX174, pBLUESCRIPT SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmids or vectors may be used as long as they are replicable in the host.

Promoter regions can be selected from any desired gene using CAT (chloramphenicol transferase) vectors or other vectors with selectable markers. Two appropriate vectors are PKK232-8 and PCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cells may be obtained using techniques known in the art. Suitable host cells include prokaryotic or lower or higher eukaryotic organisms or cell lines, for example bacterial, mammalian, yeast, or other fungi, viral, plant or insect cells. Methods for transforming or transfecting cells to express foreign DNA are well known in the art (See for example, 37, 38, and U.S. Pat. No. 4,704,362; U.S. Pat. No. 4,801,542; and U.S. Pat. No. 4,766,075), all of which are expressly incorporated herein by reference.

Introduction of the construct into the host cell can be effected by methods well known in the art such as by calcium phosphate transfection, DEAE-Dextran mediated transfection, or electroporation (39).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are known (38).

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples include the SV40 enhancer, a cytomegalovirus early promoter enhancer, the polyoma enhancer, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracelluar medium. Optionally, the heterologous sequence can encode a fusion protein including an N-terminal or C-terminal identification peptide imparting desired characteristics, e.g., stabilization or simplified purification of expressed recombinant product.

Useful expression vectors for bacterial use are constructed by inserting one or more structural DNA sequences encoding one or more desired proteins together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322, (ATCC 37017). These pBR322 "backbone" sections are combined with an appropriate promoter and the structural sequence to be expressed.

Following transformation of a suitable host strain and growth of the host strain to an appropriate cell density, the selected promoter is induced by appropriate methods (e.g., temperature shift or chemical induction) and cells are cultured for an additional period.

Cells are typically harvested by centrifugation, disrupted by physical or chemical methods, and the resulting crude extract retained for further purification. Microbial cells employed in expression of proteins can be disrupted by any convenient method, including freeze-thaw cycling, sonication, mechanical disruption, or use of cell lysing agents. Such methods are well known to a person of ordinary skill in the art.

Various mammalian cell culture systems can also be employed to express recombinant protein. Examples of mammalian expression systems include the COS-7 lines of monkey kidney fibroblasts, (40), and other cell lines capable of transcribing compatible vectors, for example, the C127, 293T, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

The Cosmc-1 polypeptides or portions thereof can be recovered and purified from recombinant cell cultures by methods including but not limited to ammonium sulfate or ethanol precipitation, acid extraction, anion or cation exchange chromatography, phosphocellulose chromatography, hydrophobic interaction chromatography, affinity chromatography, hydroxyl apatite chromatography, and lectin chromatography, alone or in combination. Protein refolding steps can be used as necessary in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

A recombinant Cosmc-1 of the invention, or functional fragment, derivative or analog thereof, may be expressed chromosomally, after integration of the Cosmc-1 coding sequence by recombination. In this regard any of a number of amplification systems may be used to achieve high levels of stable gene expression (38).

The cell into which the recombinant vector comprising the nucleic acid encoding the Cosmc-1 is cultured in an appropriate cell culture medium under conditions that provide for expression of the Cosmc-1 by the cell. If full length Cosmc-1 is expressed, the expressed protein will comprise an integral transmembrane portion. If a Cosmc-1 lacking a transmembrane domain is expressed, the expressed soluble Cosmc-1 can then be recovered from the culture according to methods well known to persons of ordinary skill in the art. Such methods are described in detail, infra.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination.

The polypeptides described herein, their fragments or other derivatives, or analogs thereof, or cells expressing them can be used as immunogens to produce antibodies thereto. These antibodies can be, for example, polyclonal or monoclonal antibodies. The present invention also includes chimeric, single chain, and humanized antibodies, as well as Fab (F(ab')2 fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by other appropriate forms of administering the polypeptides to an animal, preferably a nonhuman. The antibody so obtained will then bind the polypeptide itself. In this manner, even a sequence encoding only a fragment of the polypeptide can be used by known methods to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (32), the trioma technique, the human B-cell hybridoma technique (33), and the EBV-hybridoma technique to produce human monoclonal antibodies (34).

Techniques described for the production of single chain antibodies (U.S. Pat. No. 4,946,778) can be adapted to produce single chain antibodies to immunogenic polypeptide products of this invention.

The polyclonal or monoclonal antibodies may be labeled with a detectable marker including various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbeliferone, fluorescein, fluorescein isothiocyanate, rhodamine, dichlorotriazinylamine fluorescein, dansyl chloride or phycoerythrin; examples of luminescent materials include luminol and aequorin; and examples of suitable radioactive material include $S^{35}$, $Cu^{64}$, $Ga^{67}$, $Zr^{89}$ $Ru^{97}$, $Tc^{99m}$, $Rh^{105}$, $Pd^{109}$, $In^{111}$, $I^{123}$, $I^{125}$, $I^{131}$, $Re^{186}$, $Au^{198}$, $Au^{199}$, $Pb^{203}$, $At^{211}$, $Pb^{212}$ and $Bi^{212}$. The antibodies may also be labeled or conjugated to one partner of a ligand binding pair. Representative examples include avidin-biotin and riboflavin-riboflavin binding protein.

Methods for conjugating or labeling the antibodies discussed above with the representative labels set forth above may be readily accomplished using conventional techniques (such as described in 41, 42, and U.S. Pat. No. 4,744,981; U.S. Pat. No., 5,106,951; U.S. Pat. No. 4,018,884; U.S. Pat. No. 4,897,255; and U.S. Pat. No. 4,988,496.

Due to the degeneracy of nucleotide coding sequences, other DNA sequences which encode substantially the same amino acid sequence as a Cosmc-1 gene described herein may be used in the practice of the present invention. These include but are not limited to nucleotide sequences comprising all or portions of Cosmc-1 genes which are altered by the substitution of different codons that encode the same amino acid residue within the sequence, thus producing a silent change. Likewise, the Cosmc-1 derivatives of the invention include, but are not limited to those containing, as a primary amino acid sequence, all or part of the amino acid sequence of the Cosmc-1 protein including altered sequences in which functionally equivalent amino acid residues are substituted for residues within the sequence, resulting in a conservative amino acid substitution. For example, one or more amino acid residues within the sequence can be substituted for another amino acid of a similar polarity, which acts as a functional equivalent. Substitutions for an amino acid within the sequence may be selected from, but are not limited to, other members of the class to which the amino acid belongs (see Table I).

TABLE I

Classes of amino acids suitable for conservative substitution.

| CLASS | AMINO ACID |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

As is well known to those skilled in the art, altering any given non-critical amino acid of a protein by conservative substitution may not significantly alter the activity of that protein because the side-chain of the amino acid which is inserted into the sequence may be able to form similar bonds and contacts as the side chain of the amino acid which has been substituted for. By "conservative substitution" is meant the substitution of an amino acid by another one of the same class as exemplified by Table I.

Non-conservative substitutions (outside the classes of Table I) are also possible provided that these do not interrupt the activity of Cosmc-1 or variants thereof.

The polypeptides of the present invention may be prepared synthetically, or more suitably, they are obtained using recombinant DNA technology. Thus, the invention further provides a nucleic acid which encodes Cosmc-1 or any variants or mutations thereof as contemplated elsewhere herein.

Such nucleic acids may be incorporated into an expression vector, such as a plasmid, under the control of a promoter as understood in the art. The vector may include other structures as conventional in the art, such as signal sequences, leader sequences and enhancers, and can be used to transform a host cell, for example a prokaryotic cell such as *E. coli* or a eukaryotic cell such as an insect cell. Transformed cells can then be cultured and the polypeptide of the invention recovered therefrom, either from the cells or from the culture medium, depending upon whether the desired product is secreted from the cell or not.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The genes encoding Cosmc-1 derivatives and analogs of the invention can be produced by various methods known in the art. The manipulations which result in their production can occur at the gene or protein level. For example, the cloned Cosmc-1 gene sequence can be modified by any of numerous strategies known in the art (38). The sequence can be cleaved at appropriate sites with restriction endonuclease(s), followed by further enzymatic modification if desired, isolated, and ligated in vitro. In the production of the gene encoding a derivative or analog of Cosmc-1, care should be taken to ensure that the modified gene remains within the same translational reading frame as the Cosmc-1 coding sequence, uninterrupted by translation stop signals, in the gene region where the desired activity is encoded.

Within the context of the present invention, Cosmc-1 may include various structural forms of the primary protein which retain biological activity. For example, Cosmc-1 polypeptide may be in the form of acidic or basic salts or in neutral form. In addition, individual amino acid residues may be modified by oxidation or reduction. Furthermore, various substitutions, deletions or additions may be made to the amino acid or nucleic acid sequences, the net effect being that biological activity of Cosmc-1 is retained. Due to code degeneracy, for example, there may be considerable variation in nucleotide sequences encoding the same amino acid.

Mutations in nucleotide sequences constructed for expression of derivatives of Cosmc-1 polypeptide must preserve the reading frame phase of the coding sequences. Furthermore, the mutations will preferably not create complementary regions that could hybridize to produce secondary mRNA structures, such as loops or hairpins which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site specific mutagenesis procedures may be employed to provide an altered gene having particular codons altered according to the substitution, deletion, or insertion required. Deletions or truncations of Cosmc-1 may also be constructed by utilizing convenient restriction endonuclease sites adjacent to the desired deletion. Subsequent to restriction, overhangs may be filled in, and the DNA religated. Exemplary methods of making the alterations set forth above (38).

As noted above, a nucleic acid sequence encoding a. Cosmc-1 can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated Cosmc-1 gene product. Any technique for mutagenesis known in the art can be used, including but not limited to, in vitro site-directed mutagenesis (43,44,45,46), use of TAB® linkers (Pharmacia), etc. PCR techniques are preferred for site directed mutagenesis (47).

It is well known in the art that some DNA sequences within a larger stretch of sequence are more important than others in determining functionality. A skilled artisan can test allowable variations in sequence, without expense of undue experimentation, by well-known mutagenic techniques which include, but are not limited to, those discussed in 48, 49, and 50; by linker scanning mutagenesis (51), or by saturation mutagenesis (52). These variations may be determined by standard techniques in combination with assay methods described herein to enable those in the art to manipulate and bring into utility the functional units of upstream transcription activating sequence, promoter elements, structural genes, and polyadenylation signals. Using the methods described herein the skilled artisan can without application of undue experimentation test altered sequences within the upstream activator for retention of function. All such shortened or altered functional sequences of the activating element sequences described herein are within the scope of this invention.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other species which possess Cosmc-1 activity. The PCR amplified sequences can be examined to determine the relationship between the various Cosmc-1 genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides of the nucleic acid molecule of the invention which occur naturally, as in purified products of restriction endonuclease digest, or are produced synthetically using techniques known in the art, such as phosphotriester and phosphodiesters methods (53) or automated techniques (54). The primers are capable of acting as a point of initiation of synthesis when placed under conditions which permit the synthesis of a primer extension product which is complementary to the DNA sequence of the invention i.e., in the presence of nucleotide substrates, an agent for polymerization, such as DNA polymerase, and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using to prepare amplification products. The primer preferably contains between about 7 and 50 nucleotides.

The primers may be labeled with detectable markers which allow for detection of the amplified products. Suitable detectable markers are radioactive markers such as $P^{32}$, $S35$, $I^{125}$, and $H^3$, luminescent markers such as chemiluminescent markers, preferably luminol, and fluorescent markers, preferably dansyl chloride, fluorocein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide sequence thereof which is to be amplified. Restriction site linkers may also be incorporated into the primers, allowing for digestion of the amplified products with the appropriate restriction enzymes facilitating cloning and sequencing of the amplified product.

In an embodiment of the invention a method of determining the presence of a nucleic acid molecule having a sequence encoding a Cosmc-1, or an oligonucleotide fragment thereof in a sample, is provided comprising treating the sample with primers which are capable of amplifying the nucleic acid molecule or the predetermined oligonucleotide fragment thereof in a polymerase chain reaction to form amplified sequences, under conditions which permit the formation of amplified sequences, and assaying for amplified sequences.

The polymerase chain reaction refers to a process for amplifying a target nucleic acid sequence; (as shown, for example in 55, in U.S. Pat. No. 4,863,195 and in U.S. Pat. No. 4,683,202, each of which is incorporated herein by reference). Conditions for amplifying a nucleic acid template (56) which is also incorporated herein by reference.

It will be appreciated that other techniques such as the Ligase Chain Reaction (LCR) and NASBA may be used to amplify a nucleic acid molecule of the invention. In LCR, two primers which hybridize adjacent to each other on the target strand are ligated in the presence of the target strand to produce a complementary strand (57) and European Published Application No. 0320308, published Jun. 14, 1989. NASBA is a continuous amplification method using two primers, one incorporating a promoter sequence recognized by an RNA polymerase and the second derived from the complementary sequence of the target sequence to the first primer (U.S. Pat. No. 5,130,238).

The present invention also provides novel fusion proteins in which any of the enzymes of the present invention are fused to a polypeptide such as protein A, streptavidin, fragments of c-myc, maltose binding protein, IgG, IgM, amino acid tag, etc. In addition, it is preferred that the polypeptide fused to the enzyme of the present invention is chosen to facilitate the release of the fusion protein from a prokaryotic cell or a eukaryotic cell, into the culture medium, and to enable its (affinity) purification and possibly immobilization on a solid phase matrix.

In another embodiment, the present invention provides novel DNA sequences which encode a fusion protein according to the present invention.

The present invention also provides novel immunoassays for the detection and/or quantitation of the present enzymes in a sample. The present immunoassays utilize one or more of the present monoclonal or polyclonal antibodies which specifically bind to the present enzymes. Preferably the present immunoassays utilize a monoclonal antibody. The present immunoassay may be a competitive assay, a sandwich assay, or a displacement assay, such as those described in (58) and may rely on the signal generated by a radiolabel, a chromophore, or an enzyme, such as horseradish peroxidase.

Alterations in core 1 β3-galactosyl transferase activity have been described in Tn-syndrome (35), an exceedingly rare hematologic disorder, which has been described in probably less than 50 patients. In addition, a role for an alteration in the synthesis of the core 1 structure has been proposed as a possible etiology for IgA nephropathy syndrome, although this remains to be proven (36). Core 1 β3-galactosyl transferase has also been demonstrated to be useful in the synthesis of glycosulfopeptides which can function as inhibitors of P-selectin:PSGL-1 interactions.

Therefore, the core 1 β3-galactosyl transferase enzymes coexpressed with Cosmc-1 of the present invention can be used for in vitro synthesis of glycosulfopeptides to block selectin:ligand interactions. Other potential uses for the core 1 β3-galactosyl transferase enzymes coexpressed with Cosmc-1 of the present invention which can be envisioned include diagnostic tests for the rare Tn-syndrome or IgA, nephropathy as well as for therapy of these disorders.

The invention will be more fully understood by reference to the following methods. However, the methods are merely intended to illustrate certain embodiments of the invention and are not to be construed to limit the scope of the invention.

Methods

RT-PCR, PCR, Cloning of the RT-PCR Product and Sequencing—Total RNA and genomic DNA from $5\times10^7$ cells of Jurkat (Clone E6-1—ATCC TIB 152), Molt-4 and K562 were isolated using the TOTAL RNA ISOLATION KIT (The RNA Company) and QIAGEN DNA mini kit (Qiagen, Inc) following the manufacturer's protocols. For RT-PCR of Cosmc-1, the forward primer was 5'-CTCCATA-GAGGAGTTGTTGC-3' (SEQ ID NO: 9), the reverse primer was 5'-TCACGCTTTTCTA CCACTTC-3' (SEQ ID NO: 10). The RT-PCR was performed at one-step in 25 ml reaction containing 500 ng of total RNA, RT/Taq mix and primers (SuperScript™ One-Step RT-PCR kit—Invitrogen). cDNA synthesis was accomplished by incubating the reaction at 50° C. for 30 minutes. Following denaturation at 94° C. for 2 minutes, the amplification was accomplished by performing 35 cycles of reaction at 94° C., 30 seconds; 52° C., 1 minute; 68° C., 1.5 minutes and followed by an extension of incubation at 72° C. for 10 minutes. The RT-PCR products were analyzed on a 1% TAE agarose gel and the expected 1218 bp band was excised and the DNA was extracted from the gel using QIAQUICK GEL EXTRACTION KIT (Qiagen, Inc) according to the manufacturer's protocol. One-tenth of the product was cloned into PCR3.1(+) (Invitrogen) by TA cloning and sequenced. To examine the sequence of Cosmc-1 gene, PCR was performed in a total reaction volume of 25 ml for 40 cycles at 94° C., 4 minutes; 94° C., 30 seconds; 55° C., 1 minute; 72° C., 1.5 minutes using genomic DNA as the template. Because human Cosmc-1 contains a single exon, the same primer pair used for RT-PCR was used for PCR of Cosmc-1. The PCR product was analyzed on a 1% TAE agarose gel and the expected 1218 bp band was excised, purified and directly sequenced.

Construction of an Expression Vector Encoding C-Terminal HPC-4 Epitope Tagged Human C1β3Gal-T-A mammalian expression vector of pcDNA4 (Invitrogen) encoding C-terminal HPC-4 epitope-tagged human C1β3Gal-T was constructed using PCR for introducing the HPC-4 epitope into the cDNA. The forward primer was 5'-GCGGATC-CATGGCCTCTAAATC-3' (SEQ ID NO: 11). The reverse primer containing sequence, encoding 12 amino acids of HPC-4 epitope (EDQVDPRLIDGK) (SEQ ID NO: 13) immediately following the C-terminal proline of human C1β3Gal-T, was 5'GGAAGATCTACTTGCCGTCGAT-CAGCCTGGGGTCCACCTGGTCCTCAG-GATTTCCTAACTTCACTTTG-3' (SEQ ID NO: 12). The PCR was performed by denaturation at 94° C. for 2 minutes, amplification for 35 cycles at 94° C., 30 seconds; 50° C., 30 seconds; 72° C., 1.5 minutes using human C1β3Gal-T cDNA as the template. The expected 1144 bp of PCR product was purified on 1% TAE agarose gel and digested by Nco I and Bgl II. The expected 1128 bp DNA fragment was purified and cloned into Nco I (partially digested)/BamHI sites of pcDNA4 and its sequence confirmed. For construction of an insect cell expression vector, the PCR product was digested with BamHI and Bgl II, the 1134 bp DNA fragment was purified and cloned into BamH I site of pVL1393 (PharMingen). Thus, a baculovirus transfer vector encoding a C-terminal HPC-4 epitope-tagged human C1β3Gal-T in pVL1393 was constructed.

Construction of an Expression Vector Encoding Human C-terminal His$_6$-tagged Cosmc-1—A cDNA encoding Cosmc-1 with a C-terminal His$_6$-tag was generated by introducing the His$_6$-tag into cDNA of Comsc-1 using PCR and EST AA578739 (Genome Systems) as a template. The PCR product was subcloned into pcDNA3.1 (+) using BamHI/Xba I sites. By a similar method, a Baculovirus transfer vector encoding human C-terminal His$_6$-tagged Cosmc-1 was constructed through subcloning of the Cosmc-1 cDNA into pVL1393.

Construction of an Expression Vector Encoding Human mCosmc-1—An expression vector encoding mCosmc-1 was constructed by replacing the Hind III/Xba I fragment of wtCosmc-1 in pcDNA3.1(+) (see above) with a mutated fragment of mCosmc-1 in PCR3.1 vector generated by TA cloning of the RT-PCR of mCosmc-1 from Jurkat cells. A Baculovirus transfer vector encoding human mCosmc-1 was constructed by subcloning the cDNA of mCosmc-1 from pcDNA3.1(+) into pVL1393.

Preparation of Baculovirus—Insect cell Sf-9 cultured in 5 ml of Sf-900II SFM with 10% FBS in a T25 flask about 50 to about 60% confluence at 27° C. was co-transfected by with pVL1393 vector and Baculovirus DNA using the BaculoGold™ Transfection Kit (PharMingen) according to the manufacturer's protocol. The media containing the Baculovirus was harvested 4 days post-transfection. To make large-scale preparation of Baculovirus, Sf-9 in 25 ml of media in a T75 flask at about 60% confluence was infected with 0.25 ml of Baculovirus obtained above. The Baculovirus (media) was collected 4 days post-infection and used for expression of human C1β3Gal-T and Cosmc-1.

Preparation of HPC4-UltraLinkÔ—Twenty-five mg of HPC4 mAb were dissolved in 20 ml 0.1 M MOPS and 0.6 M sodium citrate (pH 7.5), and coupled to 0.6 gm UltraLinkÔ beads (Pierce) at room temperature for 1 h, followed by blocking with 3M ethanolamine (pH 8.5) for 1 h at room temperature. The resin was then washed with 1 M NaCl and equilibrated with 25 mM Tris-HCl (pH 7.4), 150 mM NaCl and 1 mM CaCl$_2$.

Preparation of Cells Extracts—Transfected or infected cells were resuspended in appropriate volume of 25 mM Tris-HCl buffer (pH 7.5) containing 150 mM NaCl and proteinase inhibitor cocktail (Boehringer-Mannheim) and homogenized by sonication on an ice-bath 5 seconds for 4 times. The post nuclear supernatants were obtained by centrifugation of homogenate at 700×g for 10 minutes, and the extracts were obtained by adding 1% Triton X-100 to the supernatant and solubilizing on ice for 30 minutes.

Expression of Human C1β3Gal-T and Cosmc-1 in 293T Cells-Human 293T cells in T50 flasks were transiently transfected with expression vectors encoding a C-terminal HPC-4 epitope-tagged human C1β3Gal-T and/or the expression vector encoding human C-terminal His$_6$-tagged Cosmc-1 or mCosmc-1, using FuGENE™ 6 (Boehringer Mannheim) according to the manufacturer's protocol and cultured in DMEM media containing 10% fetal calf serum. Cells were harvested 72-h post-transfection and a cell extract was prepared. One portion was assayed for C1β3Gal-T activity using GalNAcα1-O-phenyl (Sigma) as the acceptor (5), and the other portion was used for capture of Cosmc-1 on Ni-NTA-Superflow and capture of C1β3Gal-T on HPC4-beads.

Expression of Human C-terminal HPC4-epitope tagged C1β3Gal-T and C-terminal His$_6$-tagged Cosmc-1, and mCosmc-1 in Hi-5 Cells—Hi-5 insect cells were cultured in 15 ml of EX-CELL 405 media at 27° C. in a T50 flask at about 70 to about 80% confluence. For infection or co-infection of human C1β3Gal-T, Cosmc-1, and mCosmc-1, 0.75 ml of Baculovirus was added into the flask. The cells were harvested 5 days post-infection. The cell extract was prepared for assaying C1β3Gal-T activity, capture of Cosmc-1 on Ni-NTA, C1β3Gal-T capture on HPC4-beads, and for Western Blot.

Transfection of Jurkat Cell Human HPC-4 Epitope-Tagged C1β3Gal-T and Cosmc-1-Jurkat cells cultured in RPMI1640 media containing 10% fetal calf serum in T175 flasks were transiently transfected with expression vectors encoding a human HPC-4 epitope-tagged C1β3Gal-T and/or the expression vector encoding human Cosmc-1 using GENEPORTER transfection reagent (Gene Therapy Systems) according to the manufacturer's protocol. The 1:100 dilution transfection Booster and 10% FBS were added to the culture 4 hours post-transfection and cultured at 37° C. and 5% CO$_2$. Cells were harvested 72 h post-transfection, and a cell extract was prepared as above.

Capture of Human HPC-4 Epitope-Tagged C1β3Gal-T on HPC4-UltraLink—HPC4-UltraLink beads (100 ml) equilibrated with 50 mM Tris-HCl pH 7.2, 150 mM NaCl and 1 mM CaCl$_2$ were incubated with the cell extracts for overnight at 4° C. The beads were collected by centrifugation (2,000×g, 2 min) and washed three times with 50 mM Tris-HCl (pH 7.4), 1 M NaCl, and 1 mM CaCl$_2$. The beads were then washed once with equilibration buffer and directly assayed for C1β3Gal-T activity (5).

Capture of Human Cosmc-1 on Ni-NTA-Superflow-The Ni-NTA-Superflow beads (100 ml) (Qiagen, Inc.) equilibrated with the Ni-NTA washing buffer containing 50 mM NaH$_2$PO$_4$, 300 mM NaCl, 20 mM imidazole, 0.1% Triton X-100 (pH 7.8) were incubated with the cell extracts overnight at 4° C. on a rotator. The beads were washed 5 times with 1 ml of the washing buffer. One portion of the beads was removed for C1β3Gal-T enzyme assay. The bound material in the other portion was eluted with 100 ml of eluting solution (50 mM NaH$_2$PO$_4$, 300 mM NaCl, 250 mM imidazole, and 0.1% Triton X-100).

Western Blot of Human HPC4-epitope Tagged C1β3Gal-T—Ten to twenty ml of cell extract, unbound material, and 25 ml of Ni-NTA bound material were electrophoresed on a SDS-PAGE (4-20%) under reducing conditions and transferred to a nitrocellulose membrane (Bio-Rad Laboratories). After blocking with 5% milk, the membrane was incubated with 10 ml of 10 mg/ml HPC-4 mAb (IgGlat room temperature for 1 h. The membrane was then washed twice with a low salt solution (25 mM Tris-HCl, pH7.4, containing 1 mM CaCl$_2$ and 150 mM NaCl) and then washed three times with a high salt solution (25 mM Tris-HCl, pH7.4 containing 1 mM CaCl$_2$ and 500 mM NaCl). The membrane was then incubated with POD conjugated, goat anti-mouse IgG at room temperature for 1 h, washed as above with low and high salt buffers, and then incubated with 6 ml of HighSignal West Pico Chemiluminescent Substrate (Pierce) at room temperature for 1 min. The blot was exposed to a BioMax film (Kodak) and the film was developed.

Results

Figure 2:
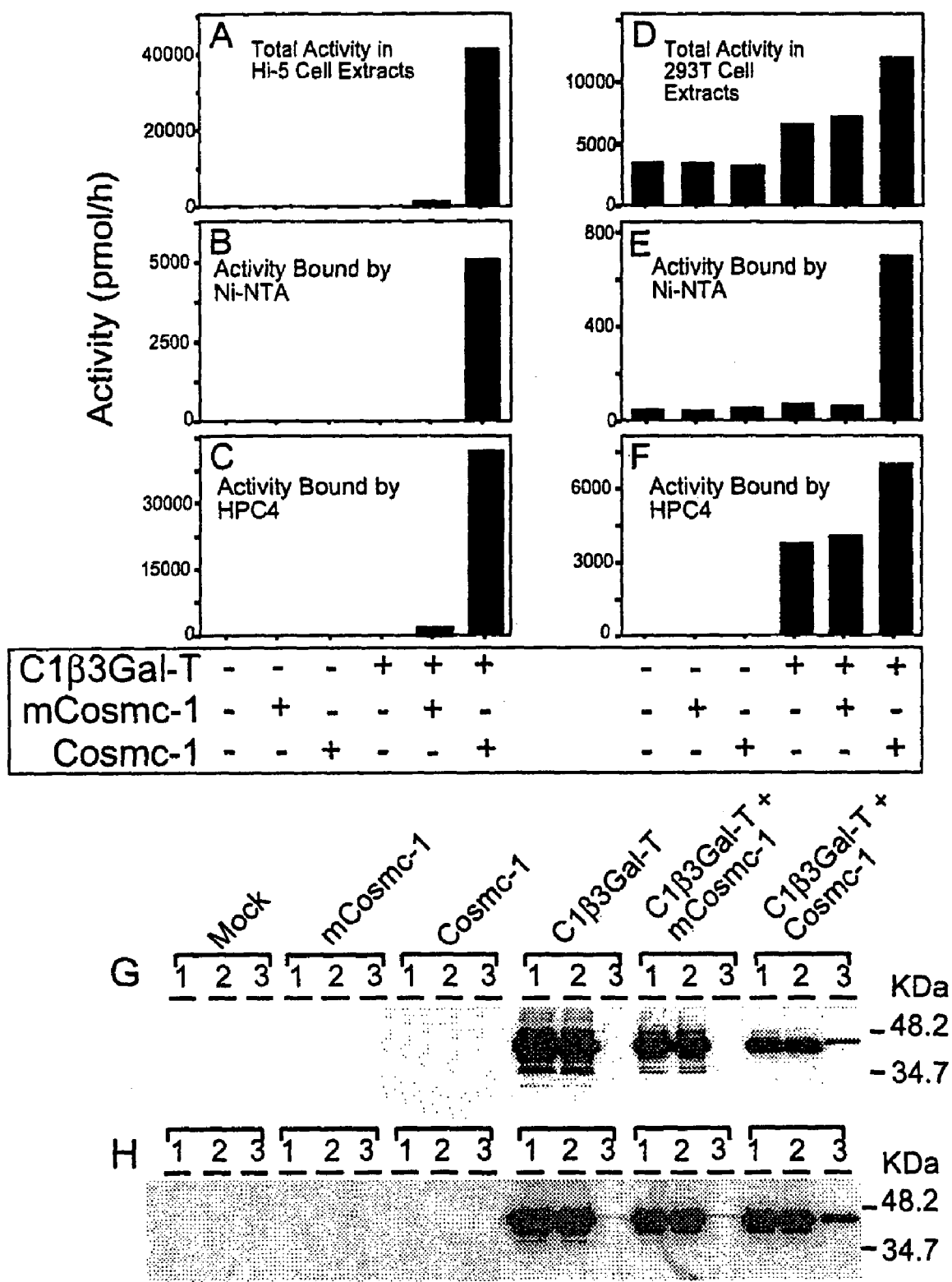
FIG. 2 depicts the requirement of wtCosmc-1, but not mCosmc-1, for the activity of human C1β3Gal-T. (A,D) The human C-terminal HPC-4 epitope-tagged C1β3Gal-T was expressed in Hi-5 cells using a baculovirus vector (A) or human 293 T cells by transient transfection (D) with or without the co-expression of wtCosmc-1 and mCosmc-1, as indicated. Infected Hi-5 cells were harvested 5 days post-infection. Extracts of the cells were prepared and total activity of C1β3Gal-T was determined. (B,E) Extracts were incubated with Ni-NTA Superflow and the total activity of bound C1β3Gal-T was determined. (C,F) Extracts were incubated with HPC4-beads and the total activity of bound C1β3Gal-T was determined. (G,H) The cell extracts either from A or D above (lane #1), the material unbound by Ni-NTA Superflow (lane #2), and the material bound by Ni-NTA Superflow (lane #3), were analyzed by SDS-PAGE (G) and Western blot (H) with monoclonal antibody to the HPC4 epitope, present at the C-terminus of the recombinant C1β3Gal-T. Molecular weight markers are indicated. The sets of lanes 1-3 from each of the cell extracts derived from different transfections (or from mock transfected cells) are indicated.
Figure 4:
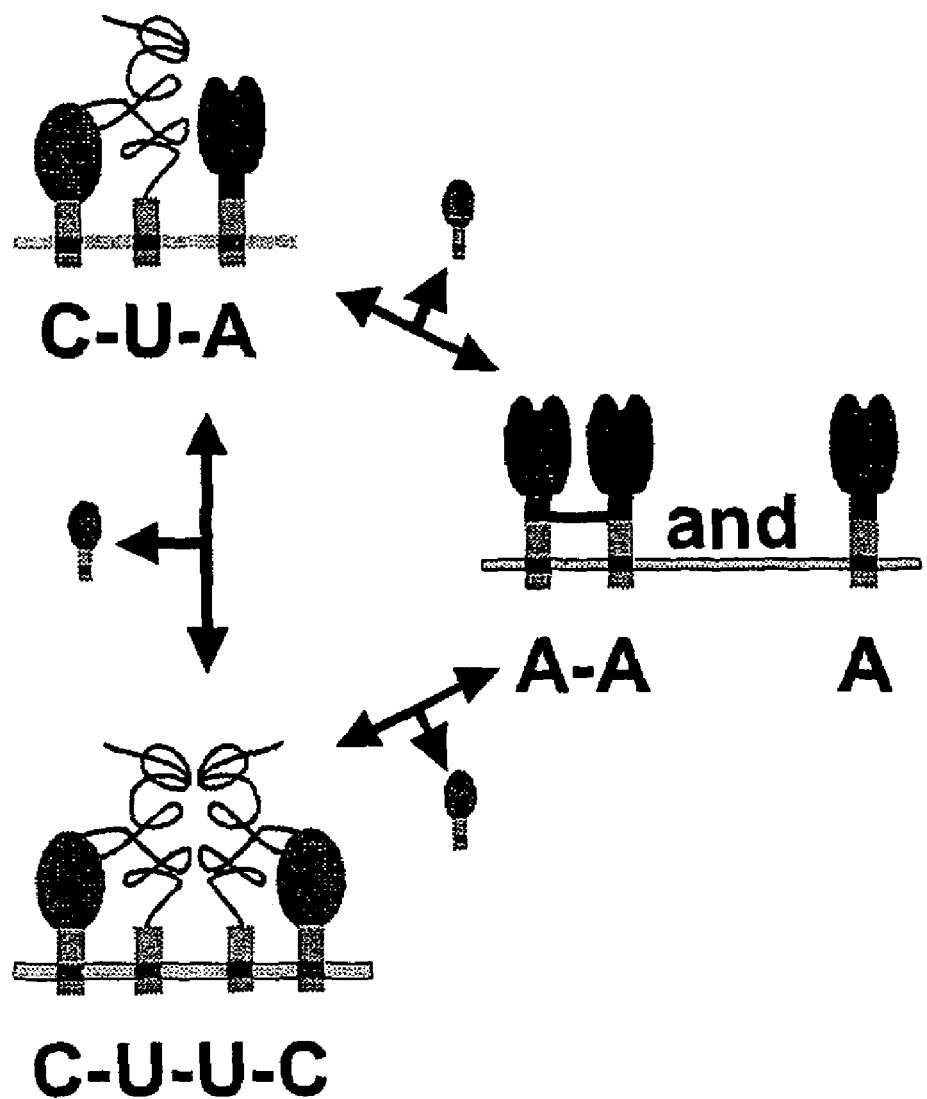
FIG. 4 depicts a model of interactions between Cosmc-1 and C1β3Gal-T in generation of active enzyme. Cosmc-1 (C) is predicted to have a chaperone function in associating with inactive C1β3Gal-T (U) in complexes either containing an active form of C1β3Gal-T (A) or lacking an active form. Potential associations of oligomeric complexes are indicated (C-U-A) and (C-U-U-C), which may co-purify as shown in FIG. 2. Following potential rounds of binding and dissociation between Cosmc-1 and C1β3Gal-T, stable active forms of the C1β3Gal-T, either dimeric (A-A) or monomeric (A), are generated. Other potential chaperones not yet defined may also be involved in formation of active C1β3Gal-T.

Results provided herein, suggest a model of how Cosmc-1 functions in the biosynthesis of the active form of C1β3Gal-T (FIG. 4). Not wishing to be constrained by theory, it will be understood that the patentability of the invention described herein does not rest on how Cosmc-1 functions to cause activation of the C1β3Gal-T. For example, Cosmc-1 may associate with folding intermediates of C1β3Bal-T, and may form a large oligomeric complex containing both native and partially unfolded forms of C1β3Gal-T (C-U-A), or may form complexes only of Cosmc-1 and unfolded C1β3Gal-T (C-U-U-C). The presence of some activity of C1β3Gal-T associated with Cosmc-1 (FIG. 2) argues for the occurrence of some mixed complexes, such as C-U-A (FIG. 4). Cosmc-1 does not appear to be associated with the soluble active form of the recombinant C1β3Gal-T, so Cosmc-1 does not appear to be a required subunit of C1β3Gal-T for its catalytic activity, which is consistent with our observation that highly purified rat liver C1β3Gal-T was also devoid of Cosmc-1 (5).

C1β3Gal-T occurs as a disulfide-bonded dimer, but monomeric forms of the enzyme may also be active (5). It is also likely that Cosmc-1 occurs in a dimeric form, based on preliminary observation in non-reducing SDS-PAGE. Thus, Cosmc-1 might associate with the C1β3Gal-T during its folding in the endoplasmic reticulum (ER). In this light it is especially interesting that recombinant HPC-4 epitope-tagged C1β3Gal-T protein does not accumulate in Jurkat cells, unless co-expressed with wild-type Cosmc-1. The recombinant HPC-4 epitope-tagged C1β3Gal-T protein can be rescued from degradation by the proteasome inhibitor lactacystin, indicating that Cosmc-1 may function by facilitating C1β3Gal-T folding/stability and trafficking out of the ER.

It is noteworthy that Jurkat cells have many other glycosyltransferases whose activities appear normal, while the primary glycosylation phenotype identified to date in these cells is the deficiency of the C1β3Gal-T activity (13). The results indicate that Cosmc-1 is a specific chaperone for C1β3Gal-T.

The mouse gene (Acc. No. NP_067525), which encodes an ortholog of human Cosmc-1, and which is hereby expressly incorporated by reference herein, was identified by others while screening a cDNA library for genes causing the growth suppression of *E. coli* (26). The authors of that study found that the protein encoded by NP_067525 had ATP binding/ATPase activity, consistent with a possible ATP-dependent chaperone function for the human Cosmc-1. The mouse Cosmc-1 protein (SEQ ID NO: 3) is predicted to contain 316 amino acids, 2 residues shorter than the human ortholog, with about 90% identity between the human and mouse Cosmc-1.

Identification of Cosmc-1. The human T-leukemic cell line Jurkat is deficient in C1β3Gal-T activity and generates truncated O-glycans bearing the Tn antigen (12, 13). We first considered the possibilities that the lack of C1β3Gal-T activity might be due to either a mutation in the C1β3Gal-T gene or transcriptional regulation of C1β3Gal-T expression. We found, however, that the transcript level for the C1β3Gal-T in Jurkat cells is much higher than that in the human lymphoblastoid cell line MOLT-4, which has relatively high levels of C1β3Gal-T activity (data not shown), and that the cDNA sequence for the C1β3Gal-T derived from Jurkat cells was normal. Thus, there is no mutation in the C1β3Gal-T gene in Jurkat cells and the cells have normal transcripts, yet lack C1β3Gal-T enzyme activity. Human C1β3Gal-T is an about 42 kDa subunit, dimeric enzyme, which is unusual in lacking common post-translational modifications, such as addition of N-glycans (4). Surprisingly, we also found that expression of a recombinant, epitope-tagged form of the enzyme in Jurkat cells, as discussed below, did not result in any detectable recombinant protein. Together, these results demonstrated that some other factor post-transcriptionally regulates expression of the C1β3Gal-T protein and enzyme activity.

A clue to this other factor was obtained by examining protein sequence data obtained during the purification of the C1β3Gal-T from rat liver. N-terminal sequences of a partially purified C1β3Gal-T, which migrated as a monomer at about 42/43 kDa and a dimer at about 84/86 kDa were obtained (5). Two amino acid sequences of different proportions were observed for the ~84/86 kDa material at each sequence cycle in the partly purified preparation. One sequence (ASKSWLNFL) (SEQ ID NO: 14) was identified as corresponding to the now defined C1β3Gal-T (4, 5), whereas the other sequence (MLSESSSFLKGVMLGSIF) (SEQ ID NO: 15) was derived from an unknown protein. A BlastP search of the NCBI EST database using this N-terminal peptide sequence identified a human EST, AA578739, which contains one open reading frame of 954 bp (FIG. 1A). A Blast search using this sequence identified a human PAC clone RP4-655L22 (Acc. Num. AC011890). This clone, derived from chromosome Xq23, contained a full-length open reading frame in a single exon. The gene present in RP4-655L22 is predicted to encode a 318 amino acid protein with type 2 membrane topology, a short cytoplasmic N-terminus, a single transmembrane domain, and a large C-terminal domain (~36.4 kDa polypeptide size), and one N-glycosylation sequon at Asn-313. Interestingly, the mature form of Cosmc-1 retains the N-terminal Met residue. A homolog of this gene was found in mice, as discussed herein, but no homologs were found in *C. elegans* or *Drosophila*. We considered whether the protein encoded by this gene was a potential accessory protein of unknown function to the C1β3Gal-T.

Figure 1D:
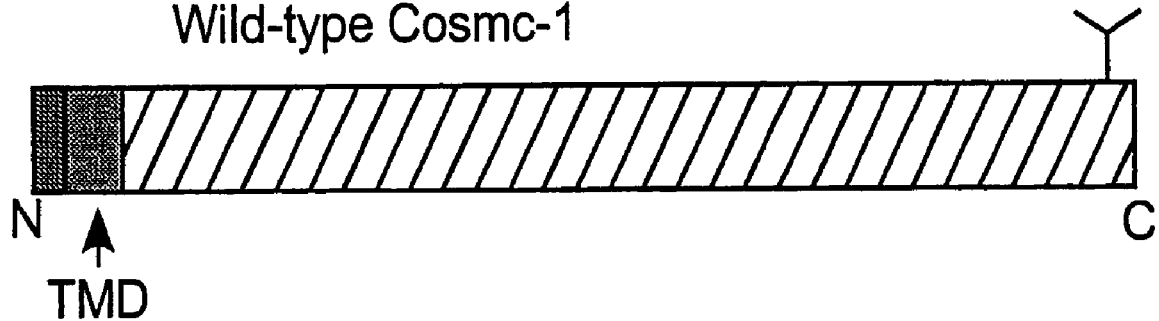
Figure 1D:
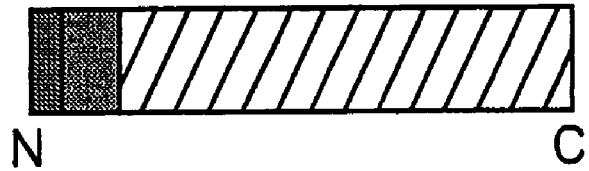

Mutation of Cosmc-1 in Jurkat Cells. We sequenced the cDNA for Cosmc-1 from Jurkat cells and identified a T-deletion at nucleotide position 478. This deletion causes a frame shift and the introduction of a stop codon (FIGS. 1B,C), resulting in a predicted mutated mCosmc-1 protein lacking most of the C-terminal domain (FIG. 1D). The Cosmc-1 gene is encoded by a single exon and we also sequenced the DNA following PCR. The DNA from Jurkat cells also encoded a single T deletion at the same position as seen in the cDNA. Jurkat cells were originally derived from a 14-yr old male (14), and since Cosmc-1 is X-linked, we would expect the cells to have only a single copy of the Cosmc-1 gene.

Chaperone Function of Cosmc-1. The mutation in Cosmc-1 in Jurkat cells and the lack of expression of C1β3Gal-T by these cells led us to test the possible chaperone function of Cosmc-1. For this we exploited our observation that expression of the human C1β3Gal-T in Hi-5 insect cells anomalously resulted in a recombinant form of the enzyme lacking activity. Insect cells have very low levels of endogenous C1β3Gal-T activity (15). For these studies we prepared epitope-tagged recombinant forms of C1β3Gal-T and Cosmc-1. A C-terminal $His_6$ tag chimeric form of wtCosmc-1 was generated (bound by Ni-NTA columns) and a C-terminal 12 amino acid HPC4 epitope-tagged chimeric form of C1β3Gal-T was generated. The HPC4 epitope is recognized by the $Ca^{2+}$-dependent mAb HPC4 (16, 17). Co-expression of wt-Cosmc-1 with the C1β3Gal-T in Hi-5 cells resulted in a substantial recovery of total enzyme activity, whereas co-expression with mCosmc-1 only slightly enhanced enzyme activity (FIG. 2A). These results demonstrate that expression of Cosmc-1 is required for the activity of human C1β3Gal-T. We also examined the potential role of Cosmc-1 expression in human 293T cells, which have an endogenous, functional C1β3Gal-T and Cosmc-1. Interestingly, activity of recombinant C1β3Gal-T was enhanced by co-expression with Cosmc-1, but not with mCosmc-1 (FIG. 2D). The higher level of activity observed by when recombinant C1β3Gal-T was co-expressed with Cosmc-1 in 293T cells, compared to the activity observed when only recombinant C1β3Gal-T expressed (FIG. 2H), raises the possibility that the endogenous levels of Cosmc-1 may be rate-limiting.

Association of Cosmc-1 and C1β3Gal-T. To directly examine whether Cosmc-1 can associate with C1β3Gal-T, we investigated whether some C1β3Gal-T activity could be bound by Ni-NTA when the HPC4-tagged C1β3Gal-T was co-expressed with $His_6$-tagged wtCosmc-1. The results show that some of the active C1β3Gal-T is co-bound with wtCosmc-1 on Ni-NTA, but not when co-expressed with mCosmc-1 in either Hi5 cells (FIG. 2B) or 293T cells (FIG. 2E). We also found that active HPC4-tagged C1β3Gal-T was recoverable from Hi-5 cells on HPC4-beads when the enzyme was co-expressed with wtCosmc-1, but much less activity (~2%) was detectable when co-expressed with mCosmc-1 (FIG. 2C). While expression of the HPC4-tagged C1β3Gal-T in 293T cells gave rise to active enzyme captured by the anti-HPC4 column, co-expression with the wtCosmc-1, but not mCosmc-1, enhanced this activity (FIG. 2F). These results demonstrate that Cosmc-1 associates with C1β3Gal-T and that expression of active C1β3Gal-T requires co-expression with wtCosmc-1.

To confirm that Cosmc-1 and C1β3Gal-T can associate, we performed Western Blots on the HPC4-tagged C1β3Gal-T expressed in Hi5 cells and 293T cells with or without $His_6$-tagged wtCosmc-1 or mCosmc-1. When HPC4-tagged C1β3Gal-T was expressed in Hi5 cells in the absence or presence of wtCosmc-1 or mCosmc-1, a considerable amount protein was generated (FIG. 2G), but the enzyme lacked activity except when co-expressed with wtCosmc-1 (FIG. 2A-C). More importantly, HPC4-tagged C1β3Gal-T was present with $His_6$-tagged wtCosmc-1 when the latter was captured on Ni-NTA (FIGS. 2G,H). By contrast, co-expression with mCosmc-1, did not result in co-isolation of HPC4-tagged C1β3Gal-T (FIGS. 2G,H). There was a slight amount of HPC4-tagged C1β3Gal-T detected in the Ni-NTA bound material in the absence of $His_6$-tagged wtCosmc-1 in 293T cells (FIG. 2H). Remarkably, this could result from co-binding of HPC4-tagged C1β3Gal-T to endogenous Cosmc-1, since the N-terminal domain of Cosmc-1 contains the sequence —H—H—H-E-H—H—H— (SEQ ID NO: 16)(FIG. 1A), which may have weak binding to Ni-NTA. This might explain why there was a low level of C1β3Gal-T activity (FIG. 2E) in the material bound by Ni-NTA in the absence of recombinant Cosmc-1 expression.

Figure 3:
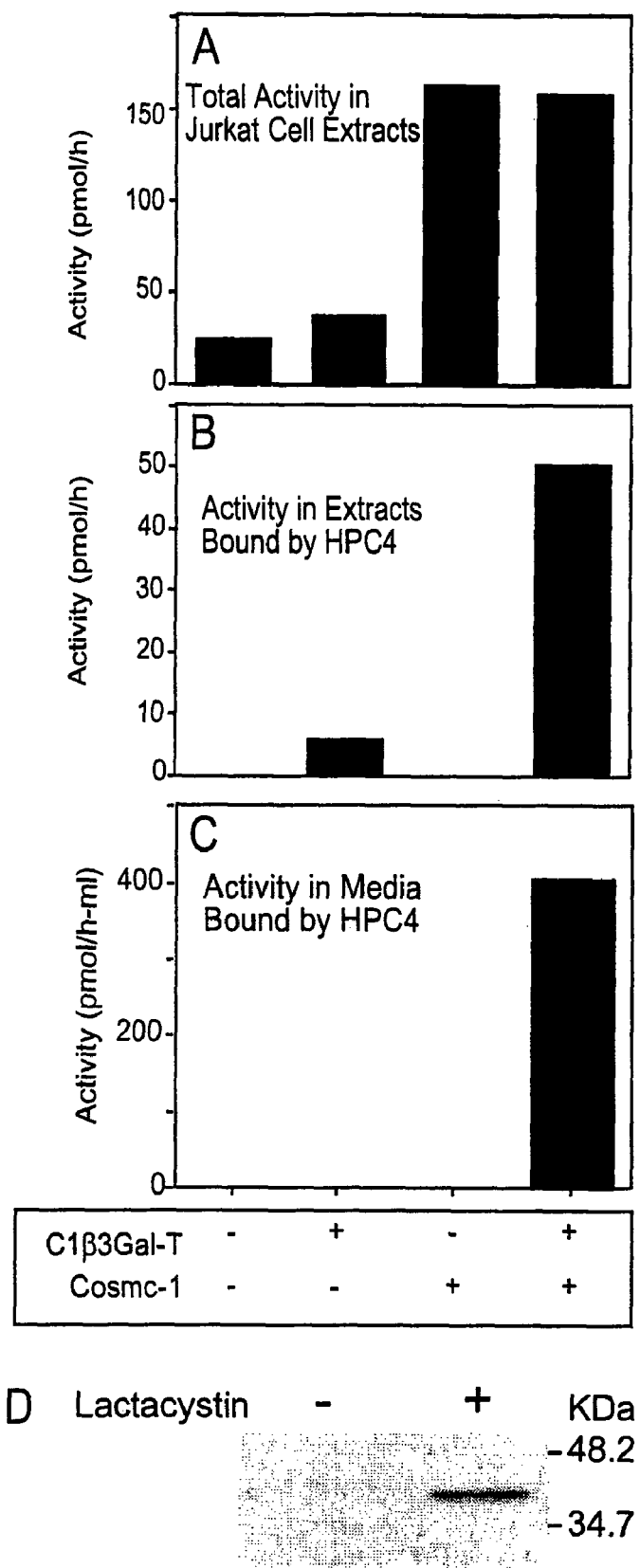
FIG. 3 depicts complementation of mCosmc-1 in Jurkat cell with wtCosmc-1. (A) Jurkat cells were transiently transfected with expression vectors encoding the full-length human C-terminal HPC-4 epitope-tagged C1β3Gal-T and/or the expression vector encoding human wtCosmc-1 (FIG. 2D). At 72 h post-transfection, cell homogenates were prepared and a portion removed for assaying activity of C1β3Gal-T. (B) A portion of the extracts was incubated with HPC4-beads and the total activity of bound C1β3Gal-T was determined. (C) Jurkat cells were stably transfected with a soluble, N-terminal HPC4-epitope-tagged form of C1β3Gal-T. The media from the cells was removed and incubated with HPC4-beads and the total activity of bound C1β3Gal-T was determined. (D) Jurkat cells stably expressing the soluble, N-terminal HPC4-epitope-tagged form of C1β3Gal-T (4) were incubated with or without lactacystin (10 mM) for 12 h. Cell extracts were then prepared, separated by SDS-PAGE, and the level of the HPC4-epitope tagged C1β3Gal-T was examined by Western blot with the HPC4 monoclonal antibody.

Complementation of Jurkat Cells by Wild-type Cosmc-1. We next tested whether wtCosmc-1 could complement the mutation of the gene observed in Jurkat cells. The C-terminal, HPC4-tagged full-length C1β3Gal-T was transiently expressed in Jurkat cells along with wtCosmc-1 and we measured the total C1β3Gal-T activity in cell extracts and HPC4-bound C1β3Gal-T from cell extracts. Expression of wtCosmc-1 in Jurkat cells enhanced the activity of the endogenous C1β3Gal-T (FIG. 3A), whereas expression of the HPC4-tagged C1β3Gal-T in the absence of wtCosmc-1 only slightly enhanced the total cellular activity (3A). These results demonstrate that Cosmc-1 can complement the defective C1β3Gal-T in Jurkat cells. Expression of full-length HPC4-tagged C1β3Gal-T in the absence of co-expressed Cosmc-1 somewhat elevated the cellular amount of HPC4-tagged C1β3Gal-T captured on HPC4-beads, but co-expression with wtCosmc-1 considerably enhanced the cellular content of HPC4-tagged C1β3Gal-T captured on HPC4-beads (FIG. 3B). We then examined the activity of a stably expressed, soluble, N-terminally HPC4-tagged C1β3Gal-T in Jurkat cells. No activity of the soluble HPC4-tagged C1β3Gal-T was detectable in media when expressed in Jurkat cells in the absence of co-expressed wtCosmc-1 (FIG. 3C), whereas co-expression with wtCosmc-1 caused the production of significant levels of C1β3Gal-T activity captured on HPC4-beads (FIG. 3C). These results demonstrate that the mutation of Cosmc-1 in Jurkat cells can be complemented by wtCosmc-1 causing elevation of endogenous C1β3Gal-T activity and in generating an active, soluble, secreted form of HPC4-tagged recombinant C1β3Gal-T. We noted that the recombinant HPC-4 epitope-tagged C1β3Gal-T protein does not accumulate in Jurkat cells in the absence of co-expressed wtCosmc-1 (FIG. 3D). Unfolded proteins in the ER are targeted for degradation by the proteasome (18). To test whether the inactive C1β3Gal-T in Jurkat cells is degraded in the ER, we treated Jurkat cells stably expressing the soluble HPC-4 epitope-tagged C1β3Gal-T with the proteasome inhibitor lactacystin (19). Treatment of these Jurkat cells with lactacystin causes a significant increase in accumulation of the tagged protein (FIG. 3D), although the recombinant protein was still an inactive enzyme (data not shown).

It will be appreciated that the invention includes nucleotide or amino acid sequences which have substantial sequence homology (identity) with the Cosmc-1 nucleotide and amino acid sequences shown in the Sequence Listings. The term "sequences having substantial sequence homology" includes those nucleotide and amino acid sequences which have slight or inconsequential sequence variations from the sequences disclosed in the Sequence Listings, i.e., the homologous sequences function in substantially the same manner to produce substantially the same polypeptides as the actual sequences. The variations may be attributable to local mutations or structural modifications.

Substantially homologous (identical) sequences are defined as including sequences having at least 90% sequence homology (identity) with the Cosmc-1 polynucleotide or polypeptide sequences shown herein or other percentages as defined elsewhere herein.

As noted elsewhere herein, the present invention includes polynucleotides comprising SEQ ID NO:2, 4, 6, and 8, and/or coding portions thereof and variant or homologous coding sequences thereof which encode the proteins of SEQ ID NO:1, 3, 5, and 7, respectively or active variants or portions thereof.

Each polynucleotide comprises untranslated regions upstream and/or downstream of the coding sequence and a coding sequence (which by convention includes the stop codon).

Figure 5:
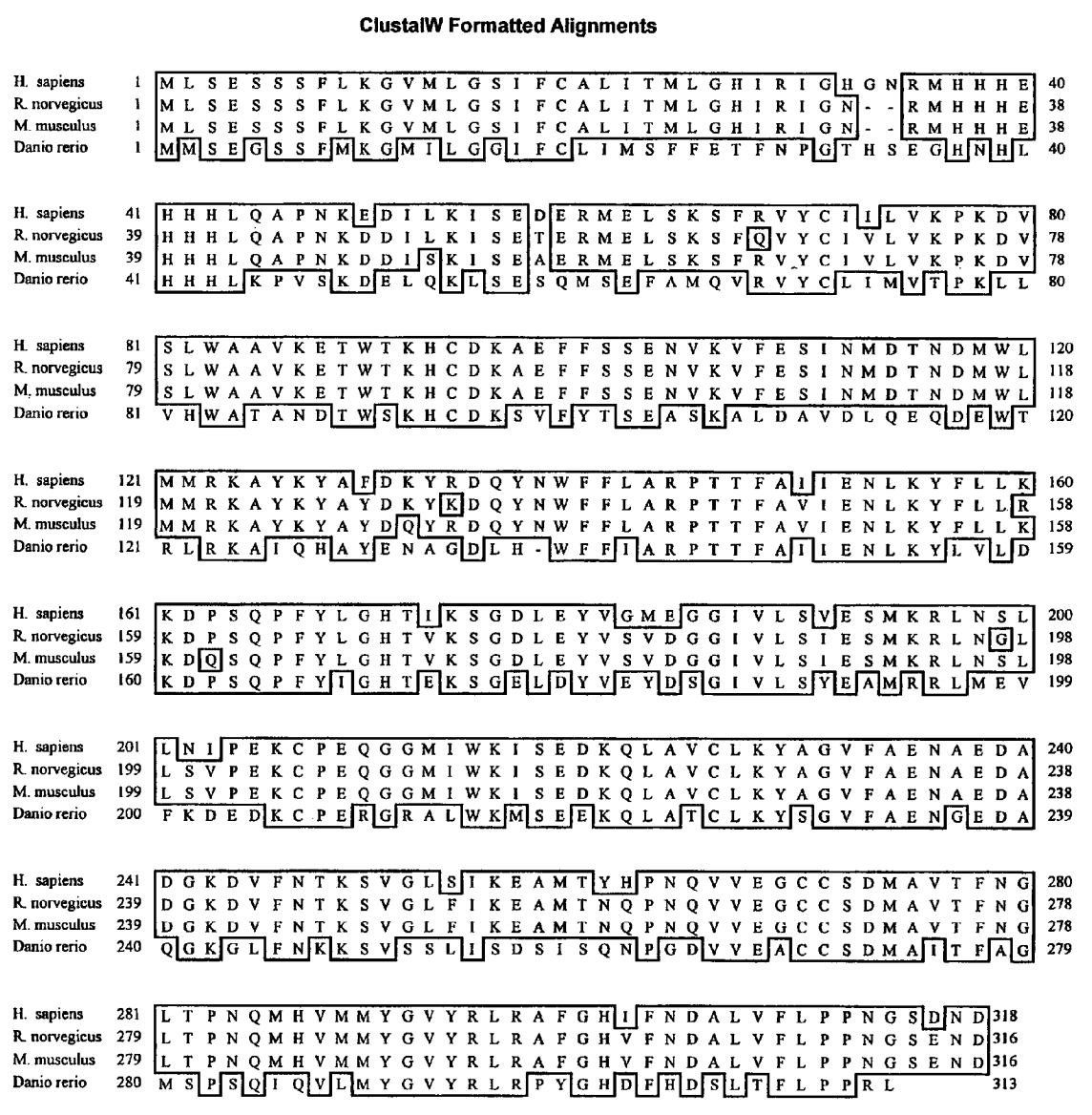

A comparison of the overall homology of the core 1 β3-GalTs identified herein further reveals a considerable range in homology (between human and mouse Cosmc-1) as indicated in the ClustalW formatted alignment in FIG. 5.

Homologies provided herein were calculated by ClustalW, a program component of MacVector Version 6.5 by the Genetics Computer Group at University Research Park, 575 Science Dr., Madison, Wis. 53711.

The term "identity" or "homology" used herein is defined by the output called "Percent Identity" of a computer alignment program called ClustalW. "Similarity" values provided herein are also provided as an output of the ClustalW program using the alignment values provided below. As noted, this program is a component of widely used package of sequence alignment and analysis programs called MacVector Version 6.5, Genetics Computer Group (GCG), Madison, Wis. The ClustalW program has two alignment variables, the gap creation penalty and the gap extension penalty, which can be modified to alter the stringency of a nucleotide and/or amino acid alignment produced by the program. The settings for open gap penalty and extend gap penalty used herein to define identity for amino acid alignments were as follows:
   Open Gap penalty=10.0
   Extend Gap penalty=0.05
   Delay Divergent=40%

The program used the BLOSUM series scoring matrix. Other parameter values used in the percent identity determination were default values previously established for the 6.5 version of the ClustalW program (59).

In general, polynucleotides which encode core 1 β3-galactosyl transferase specific molecular chaperone are contemplated by the present invention. In particular, the present invention contemplates DNA sequences having SEQ ID NO: 2, 4, 6, and 8, and/or portions or variants thereof which encode proteins having Cosmc-1 activity.

The invention further contemplates DNA sequences which comprise portions of polynucleotides of SEQ ID NO:2, 4, 6, or 8 or portions or variants thereof which encode soluble proteins having Cosmc-1 activity. That is, portions of the above polynucleotides which encode the N-terminal transmembrane region have been removed, and the remaining portions encode soluble proteins having Cosmc-1 activity.

The invention further contemplates polynucleotides which are at least about 50% homologous, 60% homologous, 70% homologous, 80% homologous or 90% homologous to the coding sequence SEQ ID NO:2, where homology is defined as strict base identity, wherein said polynucleotides encode proteins having Cosmc-1 activity.

The present invention further contemplates nucleic acid sequences which differ in the codon sequence from the nucleic acids described herein due to the degeneracy of the genetic code, which allows different nucleic acid sequences to code for the same protein as is further explained herein above and as is well known in the art. The polynucleotides contemplated herein may be DNA or RNA. The invention further comprises DNA or RNA nucleic acid sequences which are complementary to the sequences described above.

The present invention further comprises polypeptides which are encoded by the polynucleotide sequences described above. In particular, the present invention contemplates polypeptides having core 1 β3-galactosyl transferase specific molecular chaperone activity including SEQ ID NO: 1, 3, 5, and 7 and versions thereof which lack the transmembrane domain and which are therefore soluble. The present invention further contemplates polypeptides which differ in amino acid sequence from the polypeptides defined herein by substitution with functionally equivalent amino acids, resulting in what are known in the art as conservative substitutions, as discussed above herein.

Also included in the invention are polynucleotide sequences which hybridize to the coding portions of the DNAs set forth in SEQ ID NO:2, 4, 6, and/or 8 under stringent and/or relaxed conditions (as described below), and which encode proteins having Cosmc-1 activity.

Nucleic acids of the present invention are DNA sequences which hybridize to the DNA sequences which encode the Cosmc-1 or variants thereof, or their complementary sequences, under conditions of high or low stringency and which encode proteins having activity similar to the chaperone of Cosmc-1.

Hybridization and washing conditions are well known and exemplified in (38), particularly Chapter 11 and Table 11.1 therein (which are hereby expressly entirely incorporated herein by reference). The conditions of temperature and ionic strength determine the "stringency" of the hybridization.

In one embodiment, high stringency conditions are prehybridization and hybridization at 68° C., washing twice with 0.1×SSC, 0.1% SDS for 20 minutes at 22° C. and twice with 0.1×SSC, 0.1% SDS for 20 minutes at 50° C. Hybridization is preferably overnight.

In another embodiment, low stringency conditions are prehybridization and hybridization at 68° C., washing twice with 2×SSC, 0.1% SDS for 5 minutes at 22° C., and twice with 0.2×SSC, 0.1% SDS for 5 minutes at 22° C. Hybridization is preferably overnight.

In an alternative embodiment, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures.

The carrier material is then washed three times each for 15 minutes using 2×SSC, 0.2% SDS preferably at least 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

It is well known in the art that numerous equivalent conditions may be employed to comprise low stringency conditions. Factors such as the length and nature of the probe and nature of the target, and the concentration of the salts and other components (e.g., the presence or absence of formamide, dextran sulfate, polyethylene glycol) are considered and the hybridization solution may be varied to generate conditions of low stringency hybridization different form, but equivalent to, the above listed conditions. In addition, conditions which promote hybridization under conditions of high stringency (e.g., increasing the temperature of the hybridization and/or wash steps, the use of formamide in the hybridization solution) are also known in the art.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (e.e., the strength of the association between the nucleic acids) is impacted by such factors as the degree of complementary between the nucleic acids, stringency of the conditions involved, the $T_m$ (melting temperature) of the formed hybrid, and the G:C ratio within the nucleic acids. As used herein the term "stringency" is used in reference to the conditions of temperature, ionic strength, and the presence of other compounds such as organic solvents, under which nucleic acid hybridizations are conducted.

As used herein, the terms "cell," "cell line," and "cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "vector" is used in reference to nucleic acid molecules that transfer DNA segment(s) from one cell to another. The term "vehicle" is sometimes used interchangeably with "vector".

The terms "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally and operator sequence, a ribosome binding site and possibly other sequences. Eukaryotic cells are known to utilize promoters, polyadenylation signals and enhancers. It is not intended that the term be limited to any particular type of vector. Rather, it is intended that the term encompass vectors that remain autonomous within host cells (e.g., plasmids), as well as vectors that result in the integration of foreign (e.g., recombinant nucleic acid sequences) into the genome of the host cell.

The term "expression vector" and "recombinant expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is contemplated that the present invention encompasses expression vectors that are integrated into host cell genomes, as well as vectors that remain unintegrated into the host genome.

The terms "in operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The proteins contemplated herein may be expressed in either prokaryotic or eukaryotic host cells. Nucleic acid encoding the proteins may be introduced into bacterial host cells by a number of means including transformation or transfection of bacterial cells made competent for transformation by treatment with calcium chloride or by electroporation. If the proteins are to be expressed in eukaryotic host cells, nucleic acid encoding the protein or may be introduced into eukaryotic host cells by a number of means including calcium phosphate co-precipitation, spheroplast fusion, electroporation, microinjection, lipofection, protoplast fusion, and retroviral infection, for example. When the eukaryotic host cell is a yeast cell, transformation may be affected by treatment of the host cells with lithium acetate or by electroporation, for example.

Utility

In a preferred use, the invention contemplates an expression system comprising a polynucleotide encoding a recombinant core 1 β3Gal-T in a host cell in association with a polynucleotide encoding a Cosmc-1 or an effective variant thereof, wherein the core 1 β3Gal-T and Cosmc-1 or effective variant thereof can be co-expressed therein, such that the core 1 β3Gal-T which is expressed is configured into an active form of the enzyme rather than an inactive form or a form having diminished activity. The core 1 β3Gal-T can then be used within the host cell to produce O-glycans comprising core 1 structures, or the core 1 β3Gal-T can be removed and used to form core 1 O-glycans in vitro. The invention further contemplates methods of using such expression systems to form active core 1 β3GalT and/or Cosmc-1 protein, and/or protein or glycoproteins in need of synthesis of core 1 glycans thereon.

The present invention further contemplates a polyclonal or monoclonal antibody against Cosmc-1 or a variant or antigenic portion thereof as defined elsewhere herein. The monoclonal or polyclonal antibodies may be prepared by a method comprising immunizing a suitable animal or animal cell with an immunogenic Cosmc-1, variant, or immunogenic portion thereof to obtain cells for producing an antibody to said protein, fusing cells producing the antibody with cells of a suitable cell line, and selecting and cloning the resulting cells producing said antibody, or immortalizing an unfused cell line producing said antibody, e.g. by viral transformation, followed by growing the cells in a suitable medium to produce said antibody and harvesting the antibody from the growth medium in a manner well known to those of ordinary skill in the art. The recovery of the polyclonal or monoclonal antibodies may be preformed by conventional procedures well known in the art, for example as described in (32).

Antibodies may be isolated from the blood of an immunized animal or its sera by use of any suitable known method, e.g., by affinity chomatography using immobilized mutants of the invention or the mutants they are conjugated to, e.g., GST, to retain the antibodies. Similarly monoclonal antibodies may be readily prepared using known procedures to produce hybridoma cell lines expressing antibodies to peptides of the invention. Such monoclonal antibodies may also be humanized, e.g., using further known procedures which incorporate mouse monoclonal antibody light chains from antibodies raised to the mutants of the present invention with human antibody heavy chains.

In a further aspect, the invention relates to a diagnostic agent or assay component which comprises a monoclonal antibody as defined above. Although in some cases when the diagnostic agent or assay component is to be employed in an agglutination assay in which solid particles to which the antibody is coupled agglutinate in the presence of a Cosmc-1 in the sample subjected to testing, no labeling of the monoclonal antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescers, radioactive isotopes and complexing agents such as biotin. In a preferred embodiment, the diagnostic agent or assay component comprises at least one antibody covalently or non covalently bonded coupled to a solid support. This may be used in a double antibody assay in which case the antibody coupled to the solid support is not labeled. The solid support may be selected from a plastic, e.g., latex, polystyrene, polyvinylchloride, nylon, polyvinylidene difluoride, cellulose, e.g., nitrocellulose and magnetic carrier particles such as iron particle coated with polystyrene.

The monoclonal antibody of the invention may be used in a method of determining the presence of Cosmc-1 or a mutant thereof in a biological sample, the method comprising for example incubating the sample with a monoclonal antibody as described above and detecting the presence of bound toxin resulting from said incubation. The antibody may be provided with a label as explained above and/or may be bound to a solid support as exemplified above.

In a preferred embodiment of the method, a sample desired to be tested for the presence of Cosmc-1 or a mutant thereof is incubated with a first monoclonal antibody coupled to a solid support and subsequently with a second monoclonal or polyclonal antibody provided with a label. In an alternative embodiment (a so-called competitive binding assay), the sample may be incubated with a monoclonal antibody coupled to a solid support and simultaneously or subsequently with a labeled Cosmc-1 or portions thereof competing for binding sites on the antibody with any Cosmc-1 or mutant present in the sample. The sample subjected to the present method may be any sample suspected of containing a Cosmc-1 or mutant. Thus, the sample may be selected, for example, from culture supernatants, or animal body fluids (e.g., serum, colostrum or nasal mucous).

The present invention further contemplates a nucleic acid sequence encoding any of the Cosmc-1 proteins, or Cosmc-1 variants as described herein. The Cosmc-1 or variant thereof as described herein may be produced by well-known recombinant methods using cDNA encoding the Cosmc-1 or variant thereof, the cDNA having been transfected into a host cell as a plasmid or other vector.

It is clear from the above that the present invention provides compositions and methods for the production of Cosmc-1 alone or as co-expressed with Core 1β3Gal-T and for the production of polypeptides or peptides requiring glycosylation by C1β3Gal-T.

In summary, the Cosmc-1 protein or gene can be used to:
(1) Generate active recombinant forms of the C1β3Gal-T,
(2) Correct or complement the deficiency of Cosmc-1 in vertebrate or mammalian or non-vertebrate and non-mammalian cells and cell lines,
(3) Identify those cells having mutated forms of Cosmc-1,
(4) Identify those cells lacking proper levels of Cosmc-1 protein,
(5) Identify patients having mutated forms of Cosmc-1, and/or
(6) Identify patients lacking proper levels of Cosmc-1 protein.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims. It is also to be understood that all base pair sizes given for nucleotides are approximate and are used as examples for the purpose of description.

Changes may be made in the construction and the operation of the various compositions and elements described herein or in the steps or the sequence of steps of the methods described herein without departing from the spirit and scope of the invention as defined in the following claims.

Cited References:
1. Wells, L., Gao, Y., Mahoney, J. A., Vosseller, K., Chen, C., Rosen, A. & Hart, G. W. (2002) *J Biol Chem* 277, 1755-61.
2. McEver, R. P. & Cummings, R. D. (1997) *J Clin Invest* 100, S97-103.
3. Brockhausen, I., Schutzbach, J. & Kuhns, W. (1998) *Acta Anat* (Basel) 161, 36-78.
4. Ju, T., Brewer, K., D'Souza, A., Cummings, R. D. & Canfield, W. M. (2002) *J Biol Chem* 277, 178-86.
5. Ju, T., Cummings, R. D. & Canfield, W. M. (2002) *J Biol Chem* 277, 169-77.
6. Fukuda, M. & Tsuboi, S. (1999) *Biochim Biophys Acta* 1455, 205-17.
7. Springer, G. F. (1997) *J Mol Med* 75, 594-602.
8. Brockhausen, I., Yang, J., Dickinson, N., Ogata, S. & Itzkowitz, S. H. (1998) *Glycoconj J* 15, 595-603.
9. Novak, J., Julian, B. A., Tomana, M. & Mestecky, J. (2001) *J Clin Immunol* 21, 310-27.
10. Berger, E. G. (1999) *Biochim Biophys Acta* 1455, 255-68.
11. Saulsbury, F. T. (1997) *J Rheumatol* 24, 2246-9.
12. Thurnher, M., Clausen, H., Sharon, N. & Berger, E. G. (1993) *Immunol Lett* 36, 239-43.
13. Piller, V., Piller, F. & Fukuda, M. (1990) *J Biol Chem* 265, 9264-71.
14. Schneider, U. & Schwenk, H. U. (1977) *Hamatol Bluttransfus* 20, 265-9.
15. Lopez, M., Tetaert, D., Juliant, S., Gazon, M., Cerutti, M., Verbert, A. & Delannoy, P. (1999) *Biochim Biophys Acta* 1427, 49-61.
16. Stearns, D. J., Kurosawa, S., Sims, P. J., Esmon, N. L. & Esmon, C. T. (1988) *J Biol Chem* 263, 826-32. 17. Rezaie, A. R., Fiore, M. M., Neuenschwander, P. F., Esmon, C. T. & Morrissey, 3. H. (1992) *Protein Expr Purif* 3, 453-60.
18. Tsai, B., Ye, Y. & Rapoport, T. A. (2002) *Nat Rev Mol Cell Biol* 3, 246-55.
19. Fenteany, G., Standaert, R. F., Lane, W. S., Choi, S., Corey, E. J. & Schreiber, S. L. (1995) *Science* 268, 726-31.
20. Macdonald, 3. R. & Bachinger, H. P. (2001) *J Biol Chem* 276, 25399-403.
21. Ikawa, M., Nakanishi, T., Yamada, S., Wada, I., Kominami, K., Tanaka, H., Nozaki, M., Nishimune, Y. & Okabe, M. (2001) *Dev Biol* 240, 254-61.
22. Culotta, V. C., Klomp, L. W., Strain, J., Casareno, R. L., Krems, B. & Gitlin, J. D. (1997) *J Biol Chem* 272, 23469-72.
23. Ellgaard, L., Molinari, M. & Helenius, A. (1999) *Science* 286, 1882-8.
24. Buchner, J. (1999) *Trends Biochem Sci* 24, 136-41.
25. Fink, A. L. (1999) *Physiol Rev* 79, 425-49.
26. Inoue, S., Sano, H. & Ohta, M. (2000) *Biochem Biophys Res Commun* 268, 553-61.
27. Andre, P. M., Le Pogamp, P. & Chevet, D. (1990) *J Clin Lab Anal* 4,115-9.
28. Tomana, M., Matousovic, K., Julian, B. A., Radl, J., Konecny, K. & Mestecky, J. (1997) *Kidney Int* 52, 509-16.
29. Mestecky, J., Tomana, M., Crowley-Nowick, P. A., Moldoveanu, Z., Julian, B. A. & Jackson, S. (1993) *Contrib Nephrol* 104, 172-82.
30. Allen, A. C., Topham, P. S., Harper, S. J. & Feehally, J. (1997) *Nephrol Dial Transplant* 12, 701-6.
31. Schena, F. P., Cerullo, G., Rossini, M., Lanzilotta, S. G., D'Altri, C. & Manno, C. (2002) *J Am Soc Nephrol* 13, 453-60.
32. Kohler and Milstein, 1975, Nature, 256:495-497
33. Kozbor et al., 1983, Immunology Today 4:72
34. Cole, et al., 1985, in Monoclonal Antibodies and Cancer Therapy, Alan R. Liss, Inc., pp. 77-96
35. Vainchenker et al. (1985) J. Clin. Invest. 75:541
36. Kokubo et al. (1997) J. Am. Soc. Nephrol. 8:915
37. Hinnen et al., PNAS USA 75:1929-1933, 1978

38. Sambrook et al., Molecular Cloning: A Laboratory Manual 2nd Ed., Cold Spring Harbor Laboratory Press, 1989
39. Davis, L., Dibner, M. Battey, I., Basic Methods in Molecular Biology, (1986)
40. Gluzman, Cell, 23:175 (1981)
41. Inman, Methods in Enzymology, Vol. 34, Affinity Techniques, Enzyme Purification; Part B, Jacoby and Wichek (eds) Academic Press, New York, P. 30,
42. Wilcheck and Bayer, The Avidin-Biotin Complex in Bioanalytical Applications Anal. Biochem. 171:1-32, 1988
43. Hutchinson, C., et al., 1978, J. Biol. Chem. 253:6551
44. Zoller and Smith, 1984, DNA 3:479-488
45. Oliphant et al., 1986, Gene 44:177
46. Hutchinson et al., 1986, Proc. Natl. Acad. Sci. U.S.A. 83:710
47. Higuchi, 1989, "Using PCR to Engineer DNA", in PCR Technology: Principles and Applications for DNA amplification, H. Erlich, ed., Stockton Press, Chapter 6, pp. 61-70
48. D. Shortle et al. (1981) Ann. Rev. Genet. 15:265
49. M. Smith (1985) ibid. 19:423
50. D. Botstein and D. Shortle (1985) Science 229:1193
51. S. McKnight and R. Kingsbury (1982) Science 217:316
52. R. Myers et al. (1986) Science 232:613
53. Good et al., Nucl. Acid Res 4:2157, 1977
54. Conolly, B. A. Nucleic Acids Res. 15:15(8\7): 3131, 1987
55. Innis et al., Academic Pres, 1990
56. M. A. Innis and D. H. Gelfand, PCR Protocols, A Guide to Methods and Applications, M. A. Innis, D. H. Gelfand, J. J. Shinsky and T. J. White eds, pp 3-12, Academic Press 1989
57. Barney in "PCR Methods and Applications", August 1991, Vol 1(1), page 4,
58. Harlow, E. et al., *Antibodies. A Laboratory Manual*, Cold Spring Harbor Laboratory Press, Cold Spring Harbor, N.Y. (1988)
59. Thompson, J. D. et al (1994) Nucleic Acids Res 22:4673

What is claimed is:

1. An expression system comprising:
   an isolated host cell comprising:
   a first expressible recombinant polynucleotide which encodes a human core 1 β3-galactosyl transferase; and
   a second expressible recombinant polynucleotide which encodes a human core 1 β3-galactosyl transferase specific molecular chaperone for expressing the active form of the human core 1 β3-galactosyl transferase, wherein the second expressible recombinant polynucleotide comprises:
   (A) a polynucleotide having the sequence of SEQ ID NO: 2;
   (B) a polynucleotide encoding the polypeptide of SEQ ID NO: 1; or
   (C) a polynucleotide which differs in nucleotide sequence from the polynucleotides of (A) or (B) in that said polynucleotide lacks a nucleotide sequence which encodes a transmembrane domain wherein the human core 1 β3-galactosyl transferase specific molecular chaperone is soluble.

2. The expression system of claim 1 wherein the second expressible recombinant polynucleotide comprises the sequence of SEQ ID NO: 2.

3. The expression system of claim 1 wherein the first expressible polynucleotide and the second expressible recombinant polynucleotide are operatively associated with an expression control sequence.

4. The expression system of claim 1 wherein the host cell further comprises an expressible polynucleotide encoding a peptide or polypeptide requiring post-translational glycosylation to form a core 1 structure.

5. The expression system of claim 4 wherein the peptide or polypeptide requiring post-translational glycosylation to form a core 1 structure comprises P-selectin glycoprotein ligand-1 or a portion thereof which has P-selectin binding activity.

* * * * *

UNITED STATES PATENT AND TRADEMARK OFFICE
CERTIFICATE OF CORRECTION

PATENT NO. : 7,273,754 B2  Page 1 of 1
APPLICATION NO. : 10/661049
DATED : September 25, 2007
INVENTOR(S) : Richard D. Cummings and Tongzhong Ju It is certified that error appears in the above-identified patent and that said Letters Patent is hereby corrected as shown below:

Column 8, line 3: Delete "PL" and replace with -- $P_L$ --.
Column 8, line 51: Delete "lac" and replace with -- lacI --.
Column 15, line 67: Delete "nephropathy" and replace with -- nepropathy --.
Column 18, line 45: Delete "IgGlat" and replace with -- IgG1 --.
Column 28, line 31: After "Morrissey" delete "3." and replace with -- J. --.
Column 28, line 37: After "Macdonald," delete "3." and replace with -- J. --.

Signed and Sealed this

Fourth Day of December, 2007

JON W. DUDAS
*Director of the United States Patent and Trademark Office*

SEQUENCE LISTING

```
<160> NUMBER OF SEQ ID NOS: 16

<210> SEQ ID NO 1
<211> LENGTH: 318
<212> TYPE: PRT
<213> ORGANISM: Homo sapiens

<400> SEQUENCE: 1

Met Leu Ser Glu Ser Ser Ser Phe Leu Lys Gly Val Met Leu Gly Ser
1               5                   10                  15

Ile Phe Cys Ala Leu Ile Thr Met Leu Gly His Ile Arg Ile Gly His
                20                  25                  30

Gly Asn Arg Met His His His Glu His His His Leu Gln Ala Pro Asn
            35                  40                  45

Lys Glu Asp Ile Leu Lys Ile Ser Glu Asp Glu Arg Met Glu Leu Ser
    50                  55                  60

Lys Ser Phe Arg Val Tyr Cys Ile Ile Leu Val Lys Pro Lys Asp Val
65                  70                  75                  80

Ser Leu Trp Ala Ala Val Lys Glu Thr Trp Thr Lys His Cys Asp Lys
                85                  90                  95

Ala Glu Phe Phe Ser Ser Glu Asn Val Lys Val Phe Glu Ser Ile Asn
            100                 105                 110

Met Asp Thr Asn Asp Met Trp Leu Met Met Arg Lys Ala Tyr Lys Tyr
        115                 120                 125

Ala Phe Asp Lys Tyr Arg Asp Gln Tyr Asn Trp Phe Phe Leu Ala Arg
    130                 135                 140

Pro Thr Thr Phe Ala Ile Ile Glu Asn Leu Lys Tyr Phe Leu Leu Lys
145                 150                 155                 160

Lys Asp Pro Ser Gln Pro Phe Tyr Leu Gly His Thr Ile Lys Ser Gly
                165                 170                 175

Asp Leu Glu Tyr Val Gly Met Gly Gly Ile Val Leu Ser Val Glu
            180                 185                 190

Ser Met Lys Arg Leu Asn Ser Leu Leu Asn Ile Pro Glu Lys Cys Pro
        195                 200                 205

Glu Gln Gly Gly Met Ile Trp Lys Ile Ser Glu Asp Lys Gln Leu Ala
    210                 215                 220
```

```
Val Cys Leu Lys Tyr Ala Gly Val Phe Ala Glu Asn Ala Glu Asp Ala
225                 230                 235                 240

Asp Gly Lys Asp Val Phe Asn Thr Lys Ser Val Gly Leu Ser Ile Lys
                245                 250                 255

Glu Ala Met Thr Tyr His Pro Asn Gln Val Val Glu Gly Cys Cys Ser
            260                 265                 270

Asp Met Ala Val Thr Phe Asn Gly Leu Thr Pro Asn Gln Met His Val
        275                 280                 285

Met Met Tyr Gly Val Tyr Arg Leu Arg Ala Phe Gly His Ile Phe Asn
    290                 295                 300

Asp Ala Leu Val Phe Leu Pro Pro Asn Gly Ser Asp Asn Asp
305                 310                 315
```

<210> SEQ ID NO 2
<211> LENGTH: 957
<212> TYPE: DNA
<213> ORGANISM: Homo sapiens

<400> SEQUENCE: 2

```
atgctttctg aaagcagctc cttttttgaag ggtgtgatgc ttggaagcat tttctgtgct      60
ttgatcacta tgctaggaca cattaggatt ggtcatggaa atagaatgca ccaccatgag     120
catcatcacc tacaagctcc taacaaagaa gatatcttga aaatttcaga ggatgagcgc     180
atggagctca gtaagagctt tcgagtatac tgtattatcc ttgtaaaacc caagatgtg      240
agtctttggg ctgcagtaaa ggagacttgg accaaacact gtgacaaagc agagttcttc     300
agttctgaaa atgttaaagt gtttgagtca attaatatgg acacaaatga catgtggtta     360
atgatgagaa aagcttacaa atacgccttt gataagtata gagaccaata caactggttc     420
ttccttgcac gccccactac gtttgctatc attgaaaacc taaagtattt tttgttaaaa     480
aaggatccat cacagccttt ctatctaggc cacactataa aatctggaga ccttgaatat     540
gtgggtatgg aaggaggaat tgtcttaagt gtagaatcaa tgaaaagact taacagcctt     600
ctcaatatcc cagaaaagtg tcctgaacag ggagggatga tttggaagat atctgaagat     660
aaacagctag cagtttgcct gaaatatgct ggagtatttg cagaaaatgc agaagatgct     720
gatggaaaag atgtatttaa taccaaatct gttgggcttt ctattaaaga ggcaatgact     780
tatcacccca accaggtagt agaaggctgt tgttcagata tggctgttac ttttaatgga     840
ctgactccaa atcagatgca tgtgatgatg tatggggtat accgccttag ggcatttggg     900
catattttca atgatgcatt ggttttctta cctccaaatg gttctgacaa tgactga       957
```

<210> SEQ ID NO 3
<211> LENGTH: 316
<212> TYPE: PRT
<213> ORGANISM: Mus musculus

<400> SEQUENCE: 3

```
Met Leu Ser Glu Ser Ser Ser Phe Leu Lys Gly Val Met Leu Gly Ser
1               5                   10                  15

Ile Phe Cys Ala Leu Ile Thr Met Leu Gly His Ile Arg Ile Gly Asn
            20                  25                  30

Arg Met His His His Glu His His His Leu Gln Ala Pro Asn Lys Asp
        35                  40                  45

Asp Ile Ser Lys Ile Ser Glu Ala Glu Arg Met Glu Leu Ser Lys Ser
    50                  55                  60
```

```
Phe Arg Val Tyr Cys Ile Val Leu Val Lys Pro Lys Asp Val Ser Leu
 65                  70                  75                  80

Trp Ala Ala Val Lys Glu Thr Trp Thr Lys His Cys Asp Lys Ala Glu
                 85                  90                  95

Phe Phe Ser Ser Glu Asn Val Lys Val Phe Glu Ser Ile Asn Met Asp
            100                 105                 110

Thr Asn Asp Met Trp Leu Met Met Arg Lys Ala Tyr Lys Tyr Ala Tyr
        115                 120                 125

Asp Gln Tyr Arg Asp Gln Tyr Asn Trp Phe Leu Ala Arg Pro Thr
130                 135                 140

Thr Phe Ala Val Ile Glu Asn Leu Lys Tyr Phe Leu Leu Lys Lys Asp
145                 150                 155                 160

Gln Ser Gln Pro Phe Tyr Leu Gly His Thr Val Lys Ser Gly Asp Leu
                165                 170                 175

Glu Tyr Val Ser Val Asp Gly Gly Ile Val Leu Ser Ile Glu Ser Met
            180                 185                 190

Lys Arg Leu Asn Ser Leu Leu Ser Val Pro Glu Lys Cys Pro Glu Gln
        195                 200                 205

Gly Gly Met Ile Trp Lys Ile Ser Glu Asp Lys Gln Leu Ala Val Cys
    210                 215                 220

Leu Lys Tyr Ala Gly Val Phe Ala Glu Asn Ala Glu Asp Ala Asp Gly
225                 230                 235                 240

Lys Asp Val Phe Asn Thr Lys Ser Val Gly Leu Phe Ile Lys Glu Ala
                245                 250                 255

Met Thr Asn Gln Pro Asn Gln Val Val Glu Gly Cys Cys Ser Asp Met
            260                 265                 270

Ala Val Thr Phe Asn Gly Leu Thr Pro Asn Gln Met His Val Met Met
        275                 280                 285

Tyr Gly Val Tyr Arg Leu Arg Ala Phe Gly His Val Phe Asn Asp Ala
    290                 295                 300

Leu Val Phe Leu Pro Pro Asn Gly Ser Glu Asn Asp
305                 310                 315

<210> SEQ ID NO 4
<211> LENGTH: 1432
<212> TYPE: DNA
<213> ORGANISM: Mus musculus

<400> SEQUENCE: 4
cgtaacagag tgggccttgg acctctcacg tccaagcctc gtgaggcagc gctttcctgc      60
cctgaagccg ttctagatgc ggaaaaaatg ctttcagaaa gcagttcctt tttgaagggt     120
gtgatgcttg aagcatctt  ctgtgccttg atcactatgc taggccacat taggattgga     180
aacagaatgc accaccatga gcatcaccat ctgcaagccc taacaaaga  cgatatctcg     240 aaatttcag  aggctgaacg catggagctc agtaagagtt ccgggtata  ctgtatagtt     300 cttgtaaaac ccaaagatgt gagtctttgg gctgcagtga aggagacttg gaccaaacac     360
tgtgacaaag cagaattctt cagttctgaa aatgttaaag tgtttgagtc aattaatatg     420
gacacaaatg acatgtggtt gatgatgagg aaagcttaca aatatgctta tgatcaatac     480
agggaccaat acaactggtt cttccttgca cgccccacta ctttcgctgt tattgaaaac     540
ctcaaatatt ttttgttaaa aaaggatcaa tcccaacctt tctatctcgg acacactgta     600
aaatctggag accttgaata tgtgagtgtg gatggaggaa ttgtcttaag catagaatca     660
atgaaaagac tcaacagtct tctcagtgtt cctgaaaagt gtcctgaaca aggaggaatg     720
```

```
atttggaaga tatctgaaga taaacagctg gcggtctgcc tgaaatacgc cggagtattt    780
gcagaaaatg ccgaagatgc cgatggaaaa gatgtgttta ataccaaatc cgttggcctt    840
ttcattaaag aggcaatgac taaccaacca aaccaggtag tagaaggctg ttgctctgat    900
atggctgtta ctttcaatgg actgactcct aatcagatgc acgtgatgat gtatggggtg    960
taccggctta gggcatttgg acatgttttc aatgatgcat tggttttctt acctccaaat   1020
ggttctgaga atgactgaca gaaagcaaga gcatgcattt agtaactata ttcgacatg    1080 gtatcatttt taattgatga cagatctaac atagtaatat gattctttt cttatctttt    1140 acccattgaa gtctgcttgt acaatgtcaa atggaatgct gtttttccct tatatcattc   1200
ctgagaaatt aaaatgtatt aaaaataaat gttttaaaaa tagcaatttt tcaaacacat   1260
atttataagt atatttatgt gataaagact aaattataga cattgtaatc tgtggtgtat   1320
ctttgcttat tggttttaaa cttatgtatc atttagctt tgtaatatat gtaaatgaga    1380
cctctagaga atttgtgatt aaagaatact cgtagccctg aaaaaaaaa aa            1432
```

<210> SEQ ID NO 5
<211> LENGTH: 313
<212> TYPE: PRT
<213> ORGANISM: Brachydanio rerio

<400> SEQUENCE: 5

```
Met Met Ser Glu Gly Ser Ser Phe Met Lys Gly Met Ile Leu Gly Gly
1               5                   10                  15

Ile Phe Cys Leu Ile Met Ser Phe Phe Glu Thr Phe Asn Pro Gly Thr
                20                  25                  30

His Ser Glu Gly His Asn His Leu His His Leu Lys Pro Val Ser
            35                  40                  45

Lys Asp Glu Leu Gln Lys Leu Ser Glu Ser Gln Met Ser Glu Phe Ala
        50                  55                  60

Met Gln Val Arg Val Tyr Cys Leu Ile Met Val Thr Pro Lys Leu Leu
65                  70                  75                  80

Val His Trp Ala Thr Ala Asn Asp Thr Trp Ser Lys His Cys Asp Lys
                85                  90                  95

Ser Val Phe Tyr Thr Ser Glu Ala Ser Lys Ala Leu Asp Ala Val Asp
                100                 105                 110

Leu Gln Glu Gln Asp Glu Trp Thr Arg Leu Arg Lys Ala Ile Gln His
            115                 120                 125

Ala Tyr Glu Asn Ala Gly Asp Leu His Trp Phe Phe Ile Ala Arg Pro
        130                 135                 140

Thr Thr Phe Ala Ile Ile Glu Asn Leu Lys Tyr Leu Val Leu Asp Lys
145                 150                 155                 160

Asp Pro Ser Gln Pro Phe Tyr Ile Gly His Thr Glu Lys Ser Gly Glu
                165                 170                 175

Leu Asp Tyr Val Glu Tyr Asp Ser Gly Ile Val Leu Ser Tyr Glu Ala
            180                 185                 190

Met Arg Arg Leu Met Glu Val Phe Lys Asp Glu Asp Lys Cys Pro Glu
        195                 200                 205

Arg Gly Arg Ala Leu Trp Lys Met Ser Glu Glu Lys Gln Leu Ala Thr
    210                 215                 220

Cys Leu Lys Tyr Ser Gly Val Phe Ala Glu Asn Gly Glu Asp Ala Gln
225                 230                 235                 240

Gly Lys Gly Leu Phe Asn Lys Lys Ser Val Ser Ser Leu Ile Ser Asp
```

```
                    245                 250                 255
Ser Ile Ser Gln Asn Pro Gly Asp Val Val Glu Ala Cys Cys Ser Asp
            260                 265                 270

Met Ala Ile Thr Phe Ala Gly Met Ser Pro Ser Gln Ile Gln Val Leu
        275                 280                 285

Met Tyr Gly Val Tyr Arg Leu Arg Pro Tyr Gly His Asp Phe His Asp
    290                 295                 300

Ser Leu Thr Phe Leu Pro Pro Arg Leu
305                 310

<210> SEQ ID NO 6
<211> LENGTH: 1223
<212> TYPE: DNA
<213> ORGANISM: Brachydanio rerio

<400> SEQUENCE: 6
gatcactatt cttcgtcgtt aaaaggacga ctccattcta gcatgatgtc tgagggcagt      60
tcatttatga aaggcatgat cctcggagga atattctgct tgatcatgtc tttctttgag     120
acctttaatc caggaaccca ctcagaaggt cacaatcacc tccaccatca tttgaaacct     180
gtcagcaaag atgagctaca gaagttatcc gagtctcaga tgtctgagtt cgctatgcag     240
gttcgagtct actgcctcat catggtcact ccaaagcttt tagttcactg ggcgacagct     300
aacgacacct ggagcaaaca ctgcgacaaa tctgtgtttt acacctctga ggcgtctaaa     360
gctctagatg cggttgacct acaggagcag gacgagtgga caaggcttcg caaagccatc     420
caacacgctt atgagaacgc cggagacctg cactggtttt tcatagcgcg acccaccacc     480
tttgctatta tagagaatct caaatacctg gtgttggata agatccaagc cagccgtttt     540
tacattggcc acacggaaaa gtctggagag ctggattatg tggagtacga cagtgggatt     600
gtgttgagtt atgaagcgat gaggaggctg atggaggtgt ttaaagatga agataaatgt     660
ccagagcgag gacgagctct atggaagatg tctgaagaaa gcaactggc cacttgtctg      720 aagtacagcg gagtgttttgc tgaaaacgga gaggacgccc aaggcaaagg cttttttaac    780
aagaagagtg tgagctcttt gatttccgat agcatcagcc aaaacccggg cgatgtggtg     840
gaggcctgtt gttctgacat ggctatcaca tttgctggga tgtcgccgag tcagatacag     900
gtcttgatgt acggcgtcta cagacttcga ccgtacggaa cgactttca cgattccttg      960 acatttctgc ctccaagact ctgataatga ttgagggagt ttgtggattc tgaaactctt    1020
actgtgactc tcagcagtga aatgttgatc ataattgggg gcgggatgaa ttatttgtga    1080
agttggtgaa ggtaaaaatg aaaatgattt gcattatgat ttaatactaa taagtcaagt    1140
gctggatcat gtgtgtgcac ttgacagtat tttgaataaa aatgctagat tcacaaaaaa    1200 aaaaaaaaa aaaaaaaaa aaa                                              1223

<210> SEQ ID NO 7
<211> LENGTH: 316
<212> TYPE: PRT
<213> ORGANISM: Rattus norvegicus

<400> SEQUENCE: 7

Met Leu Ser Glu Ser Ser Ser Phe Leu Lys Gly Val Met Leu Gly Ser
1               5                   10                  15

Ile Phe Cys Ala Leu Ile Thr Met Leu Gly His Ile Arg Ile Gly Asn
            20                  25                  30

Arg Met His His His Glu His His His Leu Gln Ala Pro Asn Lys Asp
```

|   |   |   | 35 |   |   |   | 40 |   |   |   | 45 |   |   |
|---|---|---|---|---|---|---|---|---|---|---|---|---|---|

Asp Ile Leu Lys Ile Ser Glu Thr Glu Arg Met Glu Leu Ser Lys Ser
 50                  55                  60

Phe Gln Val Tyr Cys Ile Val Leu Val Lys Pro Lys Asp Val Ser Leu
 65                  70                  75                  80

Trp Ala Ala Val Lys Glu Thr Trp Thr Lys His Cys Asp Lys Ala Glu
                 85                  90                  95

Phe Phe Ser Ser Glu Asn Val Lys Val Phe Glu Ser Ile Asn Met Asp
             100                 105                 110

Thr Asn Asp Met Trp Leu Met Met Arg Lys Ala Tyr Lys Tyr Ala Tyr
         115                 120                 125

Asp Lys Tyr Lys Asp Gln Tyr Asn Trp Phe Phe Leu Ala Arg Pro Thr
130                 135                 140

Thr Phe Ala Val Ile Glu Asn Leu Lys Tyr Phe Leu Arg Lys Asp
145                 150                 155                 160

Pro Ser Gln Pro Phe Tyr Leu Gly His Thr Val Lys Ser Gly Asp Leu
                165                 170                 175

Glu Tyr Val Ser Val Asp Gly Gly Ile Val Leu Ser Ile Glu Ser Met
            180                 185                 190

Lys Arg Leu Asn Gly Leu Leu Ser Val Pro Glu Lys Cys Pro Glu Gln
        195                 200                 205

Gly Gly Met Ile Trp Lys Ile Ser Glu Asp Lys Gln Leu Ala Val Cys
    210                 215                 220

Leu Lys Tyr Ala Gly Val Phe Ala Glu Asn Ala Glu Asp Ala Asp Gly
225                 230                 235                 240

Lys Asp Val Phe Asn Thr Lys Ser Val Gly Leu Phe Ile Lys Glu Ala
                245                 250                 255

Met Thr Asn Gln Pro Asn Gln Val Val Glu Gly Cys Cys Ser Asp Met
            260                 265                 270

Ala Val Thr Phe Asn Gly Leu Thr Pro Asn Gln Met His Val Met Met
        275                 280                 285

Tyr Gly Val Tyr Arg Leu Arg Ala Phe Gly His Val Phe Asn Asp Ala
    290                 295                 300

Leu Val Phe Leu Pro Pro Asn Gly Ser Glu Asn Asp
305                 310                 315

<210> SEQ ID NO 8
<211> LENGTH: 1283
<212> TYPE: DNA
<213> ORGANISM: Rattus norvegicus

<400> SEQUENCE: 8
cacattagga ttggaaacag aatgcaccac catgaacatc accatctgca agccctaac      60 aaagatgata tcttgaaaat ttcagagact gaacgcatgg agcttagtaa gagtttccag     120
gtatactgta tagttctcgt aaaacctaaa gatgtgagtc tttgggctgc agtgaaggag    180
acttggacca acactgtgca aaagcagaa ttcttcagtt ctgaaaatgt taaagtgttt     240
gagtcaatta atatggacac aaatgatatg tggttgatga tgaggaaagc ttacaaatat    300
gcttatgata aatacaagga ccaatacaac tggttcttcc ttgcacgccc cactactttc    360
gctgttattg aaaatctcaa atattttttg ttaagaaagg atccatcaca acctttctat    420
ctaggtcaca ctgtaaaatc tggagaccct gaatatgtga gtgtggatgg aggaattgtc    480
ttaagcatag aatcaatgaa aagactcaat ggccttctca gtgttcctga aaagtgtcct    540

```
gaacaaggag gaatgatttg gaagatatct gaagataagc agctagcagt ctgcctgaaa    600
tatgctggag tatttgcaga aaatgcagaa gacgccgatg gaaaagatgt gtttaatacc    660
aaatctgttg gcttttcat taaagaggca atgactaacc aaccaaacca ggtagtagaa     720
ggatgttgct ctgatatggc tgttactttc aatggactga ctcctaatca gatgcatgtg    780
atgatgtatg gggtgtaccg gcttagggca tttggacatg ttttcaatga tgcattggtt    840
ttcttacctc cgaatggttc tgagaatgac tgacagaaag caagagcatg cttttagtaa    900
ctatattaag acacggtatt gttttaatt gataacaaat ctaacacagt agtatgtttc     960
tttttcttat ctggttacac tggtataatc acacattgaa gtctacttgt acattgtcaa   1020
atggaatgct gttttagcct tgcatcattt gtgagaattt aaatgtatta aaaataaatg   1080
ttttaagaat aacaatttt caaatacata tttataaata ctatatttat gtgataaaga    1140
ctaaattata gacattaaaa tctgtggtgt atctttgctt attggtttta tacctgtgta   1200
ttggggttgg ggatttagct cagtggtaga gtgcttgcct agcaagcgca aggccctggg   1260
tttggtcctt acctccgagg gaa                                           1283

<210> SEQ ID NO 9
<211> LENGTH: 20
<212> TYPE: DNA
<213> ORGANISM: Artificial sequence
<220> FEATURE:
<223> OTHER INFORMATION: Completely synthesized.

<400> SEQUENCE: 9
ctccatagag gagttgttgc                                                 20

<210> SEQ ID NO 10
<211> LENGTH: 20
<212> TYPE: DNA
<213> ORGANISM: Artificial sequence
<220> FEATURE:
<223> OTHER INFORMATION: Completely synthesized.

<400> SEQUENCE: 10
tcacgctttt ctaccacttc                                                 20

<210> SEQ ID NO 11
<211> LENGTH: 22
<212> TYPE: DNA
<213> ORGANISM: Artificial sequence
<220> FEATURE:
<223> OTHER INFORMATION: Completely synthesized.

<400> SEQUENCE: 11
gcggatccat ggcctctaaa tc                                              22

<210> SEQ ID NO 12
<211> LENGTH: 69
<212> TYPE: DNA
<213> ORGANISM: Artificial sequence
<220> FEATURE:
<223> OTHER INFORMATION: Completely synthesized.

<400> SEQUENCE: 12
ggaagatcta cttgccgtcg atcagcctgg ggtccacctg gtcctcagga tttcctaact    60
tcactttg                                                              69

<210> SEQ ID NO 13
<211> LENGTH: 12
```

```
<212> TYPE: PRT
<213> ORGANISM: Artificial sequence
<220> FEATURE:
<223> OTHER INFORMATION: Completely synthesized.

<400> SEQUENCE: 13

Glu Asp Gln Val Asp Pro Arg Leu Ile Asp Gly Lys
1               5                   10

<210> SEQ ID NO 14
<211> LENGTH: 9
<212> TYPE: PRT
<213> ORGANISM: Artificial sequence
<220> FEATURE:
<223> OTHER INFORMATION: Completely synthesized.

<400> SEQUENCE: 14

Ala Ser Lys Ser Trp Leu Asn Phe Leu
1               5

<210> SEQ ID NO 15
<211> LENGTH: 18
<212> TYPE: PRT
<213> ORGANISM: Artificial sequence
<220> FEATURE:
<223> OTHER INFORMATION: Completely synthesized.

<400> SEQUENCE: 15

Met Leu Ser Glu Ser Ser Ser Phe Leu Lys Gly Val Met Leu Gly Ser
1               5                   10                  15

Ile Phe

<210> SEQ ID NO 16
<211> LENGTH: 7
<212> TYPE: PRT
<213> ORGANISM: Artificial sequence
<220> FEATURE:
<223> OTHER INFORMATION: Completely synthesized.

<400> SEQUENCE: 16

His His His Glu His His His
1               5
```